US012758540B2

(12) United States Patent
Laforge

(10) Patent No.: US 12,758,540 B2
(45) Date of Patent: Oct. 13, 2026

(54) COMPOUND FOR PREVENTING OR TREATING A VIRAL INFECTION

(71) Applicants: INSTITUT NATIONAL DE LA SANTE ET DE LA RECHERCHE MEDICALE (INSERM), Paris (FR); UNIVERSITE PARIS CITE, Paris (FR); CENTRE NATIONAL DE LA RECHERCHE SCIENTIFIQUE, Paris (FR)

(72) Inventor: Mireille Laforge, Paris (FR)

(73) Assignees: INSERM (INSTITUT NATIONAL DE LA SANTÉ ET DE LA RECHERCHE MÉDICALE), Paris (FR); UNIVERSITE PARIS CITE, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 856 days.

(21) Appl. No.: 17/998,512

(22) PCT Filed: May 11, 2021

(86) PCT No.: PCT/EP2021/062465
§ 371 (c)(1),
(2) Date: Nov. 11, 2022

(87) PCT Pub. No.: WO2021/228846
PCT Pub. Date: Nov. 18, 2021

(65) Prior Publication Data
US 2023/0181560 A1 Jun. 15, 2023

(30) Foreign Application Priority Data
May 11, 2020 (EP) .................................... 20305465

(51) Int. Cl.
*A61K 31/47* (2006.01)
*A61K 45/06* (2006.01)
(Continued)

(52) U.S. Cl.
CPC .............. *A61K 31/47* (2013.01); *A61K 45/06* (2013.01); *A61P 31/14* (2018.01); *A61P 31/18* (2018.01)

(58) Field of Classification Search
CPC .......... A61K 31/47; A61P 31/14; A61P 31/18; A61P 31/12; A61P 31/16; A61P 31/22
See application file for complete search history.

(56) References Cited

U.S. PATENT DOCUMENTS

2010/0298209 A1 11/2010 Estaquier et al.

OTHER PUBLICATIONS

Callus et al "Caspase inhibitors: viral, cellular and chemical", Cell Death and Differentiation (2007) 14, 73-78 (Year: 2007).*
(Continued)

*Primary Examiner* — Renee Claytor
*Assistant Examiner* — Elena V Vishnyakova
(74) *Attorney, Agent, or Firm* — WCF IP

(57) ABSTRACT

The present invention relates to the use of the compound of formula (I) or its pharmaceutically acceptable salts, in the prophylaxis and/or treatment of a viral infection. It also relates to an antiviral composition comprising or consisting of at least the compound of formula (I) or one of its pharmaceutically acceptable salts, and at least one other antiviral agent; and to products comprising or consisting of at least the compound of formula (I) or one of its pharmaceutically acceptable salts, and at least one antiviral agent, as a combined preparation for simultaneous, separate or sequential use in antiviral therapy; or for simultaneous,
(Continued)

separate or sequential use for the prophylaxis and/or treatment of a viral infection.

14 Claims, 11 Drawing Sheets

Specification includes a Sequence Listing.

(51) Int. Cl.
*A61P 31/14* (2006.01)
*A61P 31/18* (2006.01)

(56) References Cited

OTHER PUBLICATIONS

Dhani et al "A long way to go: caspase inhibitors in clinical use", Cell Death and Disease (2021) 12:949 (Year: 2021).*
Poreba et al "Caspase Substrates and Inhibitors" Cold Spring Harb Perspect Biol 2013;5:a008680 (Year: 2013).*
Wang et al "Remdesivir and chloroquine effectively inhibit the recently emerged novel coronavirus (2019-nCOV) in vitro", Cell Research (2020) 30:269-271; (Year: 2020).*
Zhang et al "The use of anti-inflammatory drugs in the treatment of people with severe coronavirus disease 2019 (COVID-19): The Perspectives of clinical immunologists from China", Clinical Immunology 214 (2020) 1083932 (Year: 2020).*
Benjamin Southerland et al, "Q-VE-OPh, a Negative Control for O-phenoxy-Conjugated Caspase Inhibitors", Journal of Cell Death, vol. 3, Jan. 1, 2010.

* cited by examiner

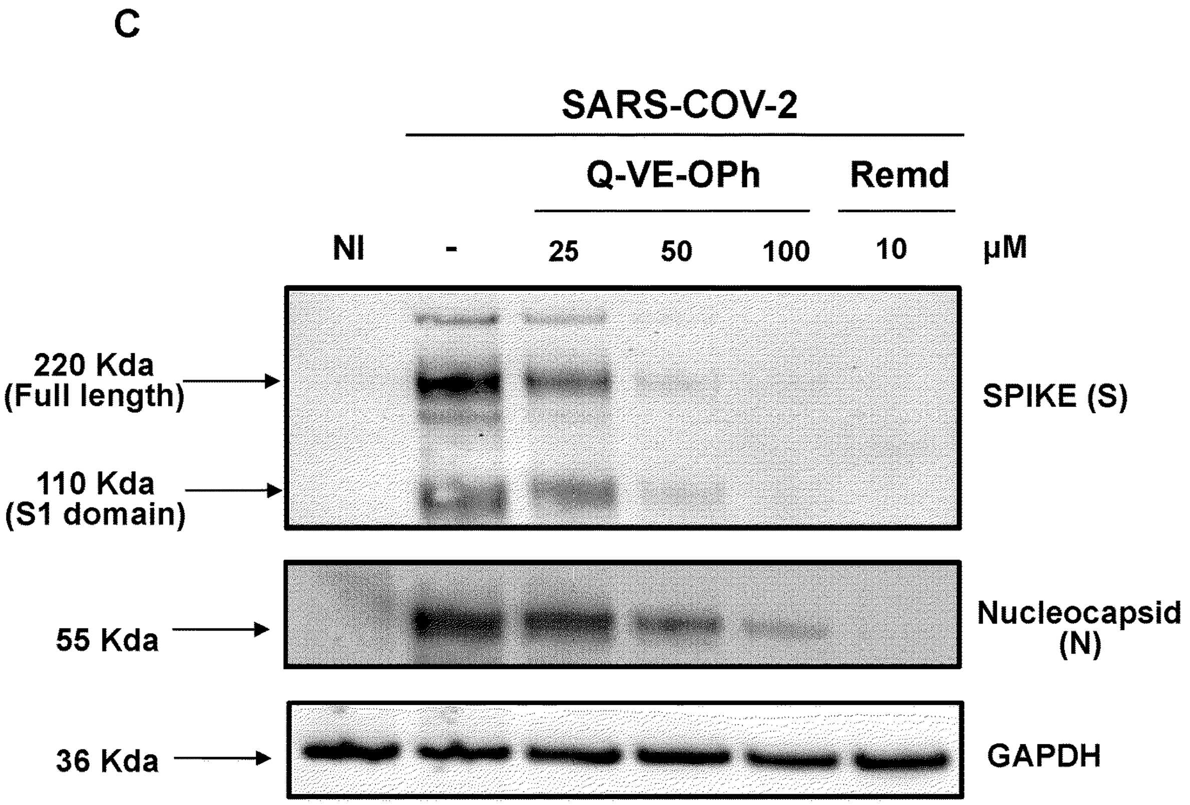
FIG.4 end

Full treatment / 72 h post-infection

A

B

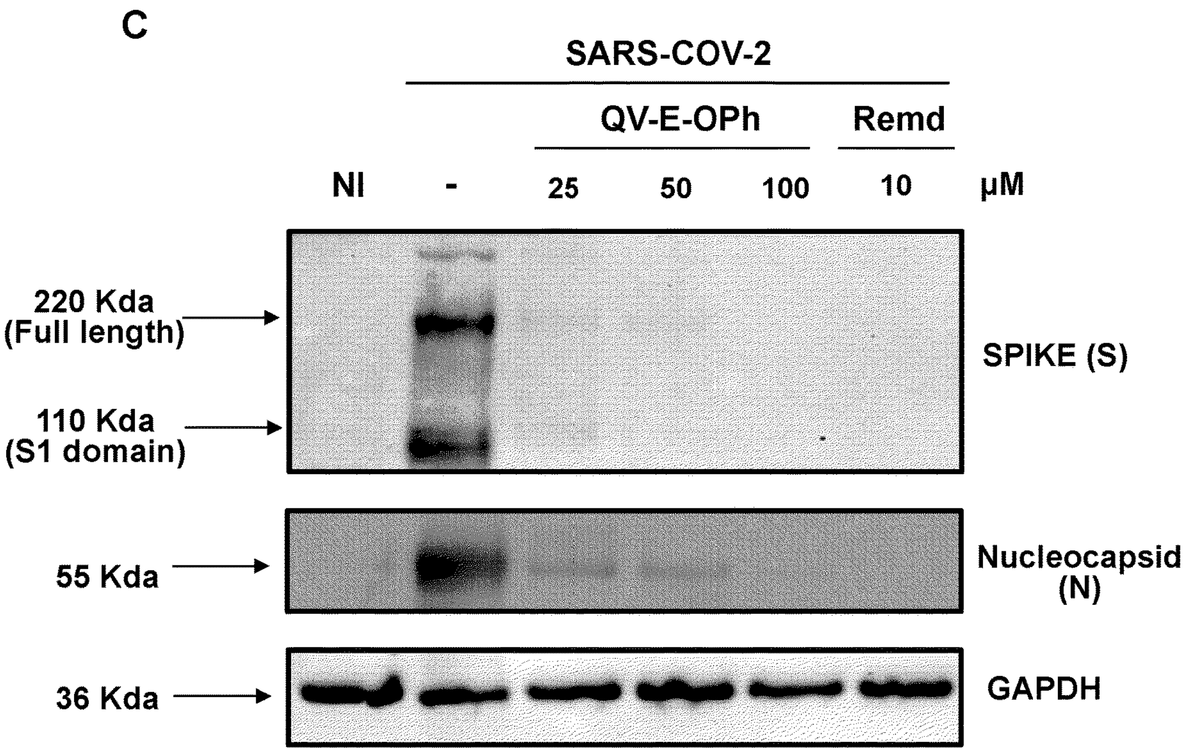
FIG.6 end

Post-Entry / 72 h post-infection

A

B

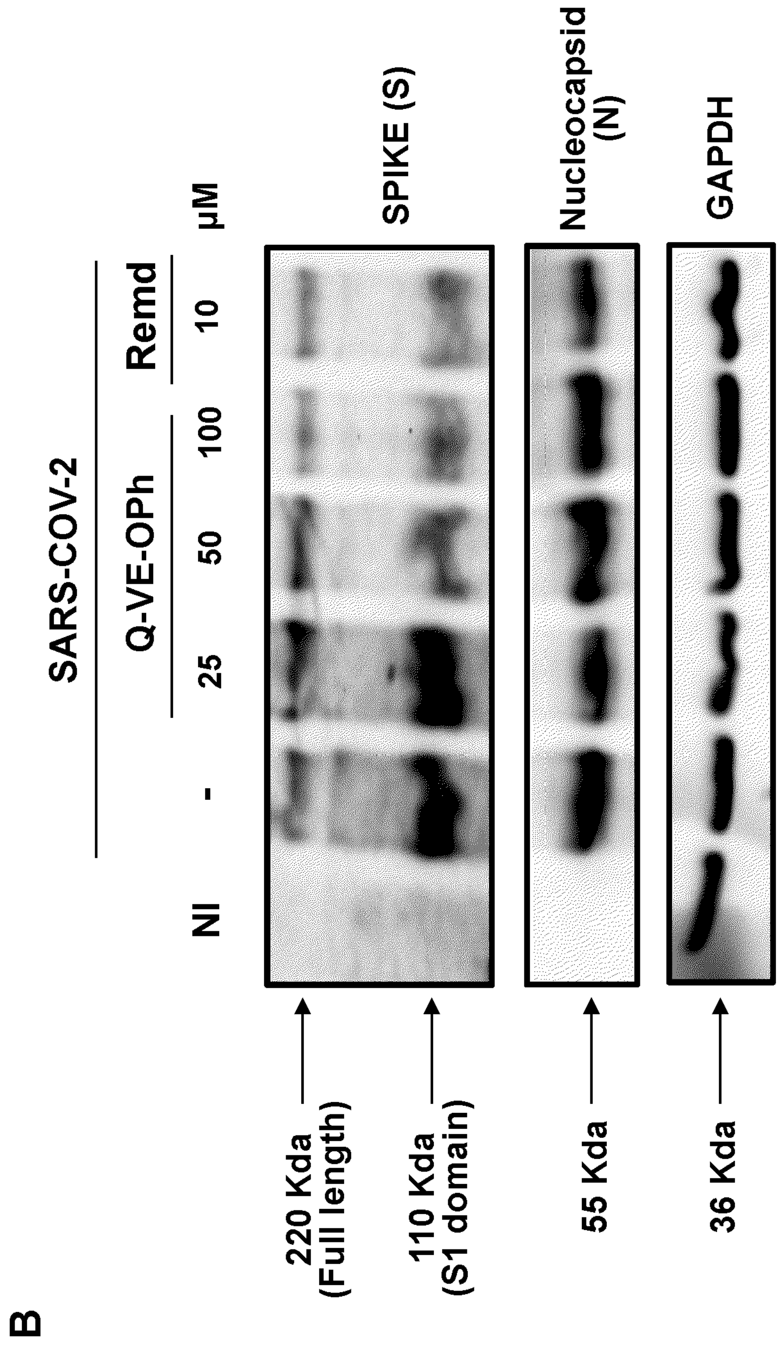
FIG.8 end

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic primer N-qF

<400> SEQUENCE: 1

cgtttggtgg accctcagat                                        20


<210> SEQ ID NO 2
<211> LENGTH: 19
<212> TYPE: DNA
<213> ORGANISM: Artificial Sequence
<220> FEATURE:
<223> OTHER INFORMATION: Synthetic primer N-qR

<400> SEQUENCE: 2

ccccactgcg ttctccatt                                         19


<210> SEQ ID NO 3
<211> LENGTH: 25
<212> TYPE: DNA
<213> ORGANISM: Artificial Sequence
<220> FEATURE:
```

-continued

<223> OTHER INFORMATION: Synthetic primer NSP6-qF

<400> SEQUENCE: 3
ggttgatact agtttgtctg gtttt 25

<210> SEQ ID NO 4
<211> LENGTH: 24
<212> TYPE: DNA
<213> ORGANISM: Artificial Sequence
<220> FEATURE:
<223> OTHER INFORMATION: Synthetic primer NSP6-qR

<400> SEQUENCE: 4
aacgagtgtc aagacattca taag 24

COMPOUND FOR PREVENTING OR TREATING A VIRAL INFECTION

The invention relates to the treatment of viral infections and to medicaments for the prophylaxis and/or treatment of viral infections, especially riboviral infections, notably retroviral and/or coronavirus infections.

Viral replication is the process by which a virus (DNA or RNA) hijacks and uses the machinery of the cell it infects to multiply. By way of example, the main steps of the replication of retroviruses, and in particular of HIV viruses, are as follows:

(1) fixing of the virus to the surface of a cell of an animal or human organism by recognition between virus surface proteins and receptors at the surface of said cell (for example the CD4 receptor);
(2) penetration of the virus into the cell cytoplasm by fusion of the virus envelope with the cell membrane;
(3) decapsidation of the virus (the virus separates from the matrix and from the capsid, which releases the two copies of the viral genome);
(4) reverse transcription of the viral RNAs in the form of a proviral DNA by virtue of reverse transcriptase (viral enzyme);
(5) migration of the proviral DNA into the nucleus and integration of that DNA into the DNA of the host cell under the effect of integrase (viral enzyme);
(6) transcription of the DNA of the cell into genomic RNA (unspliced messenger RNA (mRNA)) under the effect of the RNA polymerase of the cell;
(7) splicing of the mRNA, by excision of the introns, to leave only the exons (which code for the proteins Gag, Pol and Env);
(8) translation, in the rough endoplasmic reticulum, of the mRNA in the form of polypeptides;
(9) maturation of the polypeptides in the Golgi apparatus, allowing functional polypeptides to be obtained;
(10) assembly of the viral particles at the surface of the membrane by accumulation of the multimerized structural polyproteins (Gag, p55), the viral nonstructural proteins (reverse transcriptase, integrase, protease) and the viral RNAs;
(11) release of the virions by budding at the surface of the infected cell; and finally
(12) maturation of the viruses.

The same kind of mechanism is used by coronaviruses, except notably the reverse transcription, migration and transcription steps: they fix to the surface of a cell of an animal or human organism by recognition between their surface proteins and receptors at the surface of said cell (in this case it may be in particular ACE2 and/or TMPRSS2).

Viruses have developed various strategies for escaping the immune system and facilitating their dissemination during the infection. In particular, the HIV virus has the particular feature of causing the complete breakdown of the immune system by attacking a key cell of the immune system, the auxiliary T lymphocyte (CD4+T lymphocyte), which expresses at its surface the CD4 molecule, a specific HIV receptor. The monocytes-macrophages, the dendritic cells, the Langerhans cells and the cerebral microglial cells are likewise targets of HIV. The gradual disappearance of the lymphocytes leads to a lack of control of viral replication by the immune system, to the destruction of the lymphoid organs, where the immune response takes place, and to the onset of acquired immunodeficiency syndrome (AIDS), with the occurrence of severe opportunistic infections. The mechanisms responsible for the disappearance of the CD4+T lymphocytes during infection by HIV are complex, and they have been elucidated only partially.

The HIV viral particle is composed of a nucleocapsid which contains the single-stranded RNA dimer of positive polarity associated with the nucleocapsid protein, lysine tRNAs and the viral enzymes (reverse transcriptase, protease and integrase). The nucleocapsid is enclosed in a coat of matrix proteins which is covered by a lipid membrane borrowed from the host cell during budding of the viral particle. The membrane is provided with spikes composed of envelope glycoprotein oligomers. The step of conversion of the RNA into bicatenary DNA during the viral cycle under the action of a viral enzyme, reverse transcriptase, is the main characteristic of the retroviruses.

The viral genes gag, pol and env are retained in all retroviruses. All the products derived therefrom are present in the viral particle. They come from the cleavage of precursor polyproteins. The genes gag and env code for structural proteins, and the gene pol codes for numerous enzymatic proteins.

The Gag proteins are obtained from the cleavage of the polyprotein Pr55gag by viral protease. The cleavage releases the matrix protein, the capsid protein, the nucleocapsid protein, as well as a 6 kDa protein.

The envelope precursor gp160 is cleaved into a surface glycoprotein gp120 (gp130 for SIVmac) and a transmembrane protein gp41 derived from the C-terminal region of the precursor. During its maturation, the precursor gp160 is glycosylated and then cleaved by a cell protease in the Golgi apparatus and then exported to the plasmic membrane. The two glycoproteins derived from the cleavage remain associated by non-covalent bonds. They form heteromers of envelope glycoproteins, which combine in oligomers to form the spikes of the virion.

The gene pool codes for three enzyme proteins: protease, reverse transcriptase and integrase. They are derived from the cleavage of the polyprotein Gag-Pol (Pr160 gag-pol) during the morphogenesis of the virion. Dimerization in the cell of the polyprotein Gag-Pol reveals the protease activity coded for by the 5'-region of pol. The mature form of the protease, released by autocatalytic cleavage, remains in the dimeric form p11/p11 and is then able to cleave other sites present on the polyproteins Pr160gag-pol and Pr55gag.

Reverse transcriptase is derived from the cleavage of the polyprotein Pr160gag-pol in two steps by the viral protease during the assembly of the viral particle.

Located in the C-terminal position of the Pol region of the polyprotein Gag-Pol, integrase is released in the form of a 32 kDa protein under the action of the viral protease. Its oligomerization is required both for its incorporation into the viral particle and to exert its activity of integrating linear double-stranded viral DNA into the cell genome.

All of these works emphasize the major role of protease(s) in the genesis of an infectious viral particle. Accordingly, as well as using retrotranscriptase inhibitors or nucleoside analogues, the HIV therapy known as highly active antiretroviral therapy or "HAART" today includes one or more HIV protease inhibitors. This therapy leads to inhibition of viral replication, an increase in the number of CD4 T lymphocytes and an indisputable clinical improvement.

However, insofar as no current treatment enables patients to be cured of AIDS, and HIV virus isolates are or are becoming resistant to existing treatments, it is of major interest to find antiviral molecules which allow viral infections in general and infections by retroviruses such as HIV in particular to be combated more effectively.

Many viral infections coincide with disturbances in the mechanisms that control cell death. Apoptosis (or programmed cell death or even cell suicide) is the process by which cells trigger their self-destruction in response to a signal (pro-apoptotic signal). Apoptosis is a morphologically and biochemically defined form of cell death which is characterized in vivo by the absence of an inflammatory response, the activation of caspases and the cleavage of numerous proteins, fragmentation of the DNA, condensation of chromatin, cell contraction and the disassembly of cell structures to form vesicles incorporated into the membrane (apoptotic bodies). In vivo, this process culminates in the phagocytosis of apoptotic bodies by other cells.

Precocious apoptosis of a cell infected by a virus can constitute a defence mechanism of the host; it allows the number of viral particles released to be limited by interrupting viral replication. The cell endonucleases produced during apoptosis can act on the viral DNA and inhibit the synthesis of viral, structural and regulatory proteins and the formation of infectious viral particles, thus limiting the dissemination of virions in the host.

Accordingly, many viruses act on the regulation of the apoptotic intracellular signals, either in order to keep themselves alive or to keep the infected cell viable or to prevent the cell from being attacked by the effector cells of the immune system, and thus increase the efficacy of viral replication and permit greater production of virions.

Other viruses, on the other hand, have also developed strategies for causing the death of the cells they infect, leading to cell deficiencies, in particular immune deficiencies (such as those associated with AIDS), neuronal deficiencies (such as those associated with rabies) and epithelial deficiencies (such as those associated with haemorrhagic fevers). In the case of immune deficiencies alone, the viruses are then able to propagate. Some viruses are additionally capable of inducing apoptosis at a late phase of the infection, which allows the virions to propagate into the neighbouring cells while escaping the inflammatory and immune response of the host.

One of the major components of the machinery of apoptosis is a family of cysteine proteases called caspases (from the English cysteinyl aspartate-specific proteases or cysteine aspartate proteases). Caspases have been found in many organisms, ranging from *C. elegans* to humans. To date, more than about twelve caspases have been identified. These intracellular enzymes have a key role in apoptosis, inflammation, activation and cell differentiation.

The function of the caspases is determined by their substrate specificity, the length of their prodomain and the sequence of the prodomain. The caspases can be divided into three groups: the inflammatory caspases (group I), the initiator (or regulatory) caspases (group II) and the effector (or executor) caspases (group III) (Lavrik et al., 2005). The inflammatory caspases include caspase-1, -4, -5, -11, -12, -13 and -14. They are involved in the inflammatory processes and play a central role in the activation of certain cytokines. The initiator caspases include caspase-2, -8, -9 and -10. They are located upstream of the apoptotic signalling cascades and are activated by autoproteolytic mechanisms in response to proapoptotic signals. They then cleave and activate the effector caspases, which are located downstream of the signalling cascades, permitting amplification of the apoptotic signal. The effector caspases include caspase-3, -6 and -7. They are involved directly in the execution or occurrence of apoptosis; once activated by the initiator caspases, they cleave numerous cell proteins, thus leading to dismantling of the cell or inactivation of other proteins. The proteins inactivated by the action of these caspases (approximately from 2000 to 3000 substrates) include proteins which protect the cells from apoptosis (antiapoptotic proteins), such as proteins of the Bcl-2 family.

The preferences or substrate specificities of individual caspases have been used to develop peptides which effectively enter into competition with the binding of the caspases to their substrate. These caspase inhibitors are capable of penetrating the cells and binding irreversibly (with the exception of inhibitors having an aldehyde group, whose binding is reversible) to the active site of the caspases. They accordingly act as proteolytic decoys by blocking proteolytic caspase cleavage, which is required for activation of said caspases and the production of an active truncated caspase.

Among the different caspase inhibitors which are commercially available, the caspase inhibitor Q-VD-OPh (N-(2 (quinolyl)valyl-aspartyl-(2,6-difluorophenoxy)methyl ketone; caspase inhibitor ab141421 of abcam or 1170 of Biovision) is interesting because of its increased efficacy, stability and permeability, and reduced toxicity (even when used in a high concentration and for a period of 4 months daily, see Chanel L. I. Keoni and Thomas L. Brown, Journal of Cell Death, 2015) as compared with inhibitors having a carboxy-terminal group of the fluoromethyl ketone (fmk) type. Said inhibitor Q-VD-OPh has been shown to inhibit various caspases, in particular caspase-1, -3, -8, -9, -10 and -12.

Besides, patent application WO2009/092897 discloses that said compound Q-VD-OPh not only permits inhibition of the apoptotic phenotype (caspase inhibition, DNA condensation and fragmentation) of the HIV-infected cells, but also inhibition of their death and especially inhibition of viral replication. Said compound Q-VD-OPh may be used as an antiviral agent, because of its combined properties of inhibiting viral replication and of inhibiting caspases.

More recently, Laforge et al (Journ Clin Invest, Volume 128, Number 4, April 2018, 1627-1640) have shown that a treatment with the compound Q-VD-OPh prevents AIDS disease progression in SIV-infected rhesus macaques and allows a long-term control of viral replication, thanks to the caspase inhibitor properties of said molecule. After treatment of six monkeys with five injections of said compound during primary infection, none of the animals have developed a cancer even after four or five years after treatment.

It results that research has been focused on developing antiviral agents, such as Q-VD-OPh, based on their action on caspases, and finally on apoptosis. However, the spectrum of said agents is limited.

Moreover, a long-term administration or treatment with Q-VD-OPh for a long period could be harmful. Indeed the administration for years, and in a repeated manner, could lead to severe adverse events and/or other pathologies, such as cancer. The benefit of the treatment by Q-VD-OPh on apoptosis has been shown during primary-infection in non-human primate model infected by SIV (i.e. when apoptosis is at its maximum level).

There is thus still a need for antiviral agents which would encompass a broad spectrum of action. Especially, there is a need for antiviral agents which would be effective in inhibiting viral replication, independently of any caspase inhibition. Such agents would be specific for their antiviral action. There is also a need for antiviral agents which would be safe, i.e. not toxic with a long-term administration, which would have no action on caspase inhibition and thus on apoptosis. Such antiviral agents would be effective especially for a long-term treatment, notably effective thanks to the penetration of said antiviral agents into the different lymphoid organs—such as peripheral lymphoid organs and mesenteric ganglions, which are viral reservoirs. Such antiviral agents may also go through the blood-brain barrier, and have access to the brain, which may also be a viral reservoir.

The present invention solves this problem: the inventors have surprisingly discovered that a specific molecule, which is structurally very close to Q-VD-OPh, inhibits viral replication, and has no effect on caspase inhibition. Said compound is thus specific for its antiviral action, and has no action on caspase inhibition and thus on apoptosis. Said compound is the compound of formula (I) below. As shown in example 1, this compound of formula (I) inhibits viral replication, particularly HIV replication, and this mechanism is independent from caspase inhibition. As shown in example 2, this compound of formula (I) is also able to control SARS-CoV-2 infection, and inhibits SARS-CoV-2 viral replication inside the cell, and prevents viral production and new infections without any toxicity.

The invention accordingly relates to a compound chosen from the compound of formula (I) and its pharmaceutically acceptable salts:

(I)

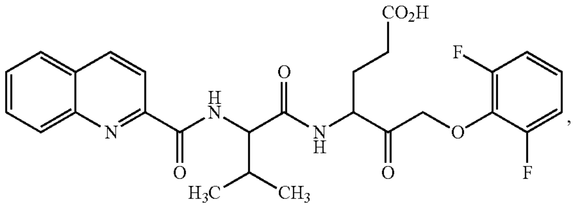

, for use as an antiviral agent and more particularly as an anti-riboviral agent. Said compound is used in particular for the prophylaxis and/or treatment of a viral infection, in particular in an animal or human, and more particularly for inhibiting viral replication in an animal or human infected by a virus.

The compound of formula (I) is also called "Q-VD-OPh negative control" or "Q-VE-OPh" in the present application. The chemical name of said compound is N-(2(quinolyl)-L-valyl-L-glutamyl-(2,6-difluorophenoxy)methyl ketone. It is also called Quinolyl-Val-Glu-OPh. It is commercially available under the name Q-VD-OPh negative control, caspase inhibitor ab141389 from abcam or 1171 from Biovision.

The invention also relates to a composition comprising, as active ingredient, a compound according to the invention and further comprising one or more carrier(s), diluent(s) or adjuvant(s) or a combination thereof, for use in the prophylaxis and/or treatment of a viral infection.

The invention also relates to an antiviral composition comprising or consisting of:

(i) at least one compound chosen from the compound of formula (I) and its pharmaceutically acceptable salts:

(I)

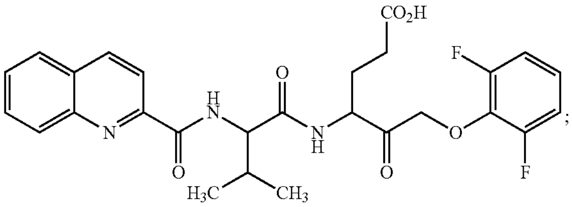

;

and (ii) at least one antiviral or anti-inflammatory agent, in particular at least one antiretroviral agent, wherein said antiviral agent is different from (i).

The invention also relates to products comprising or consisting of:

(i) at least one compound chosen from the compound of formula (I) and its pharmaceutically acceptable salts:

(I)

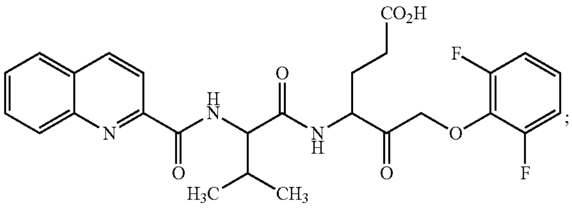

;

and (ii) at least one antiviral or anti-inflammatory agent, in particular at least one antiretroviral agent, wherein said antiviral agent is different from (i), as a combined preparation for simultaneous, separate or sequential use in antiviral therapy; or for simultaneous, separate or sequential use for the prophylaxis and/or treatment of a viral infection.

Unless indicated otherwise, each embodiment indicated in this application applies independently and/or in combination with the other embodiments described.

By "pharmaceutically acceptable salt", it is meant any pharmaceutically acceptable salt of a compound of formula (I) derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002. Preferably, the pharmaceutically acceptable salt is a chlorhydrate salt. Such a salt may be obtained by using HCl. More preferably, one of the nitrogen atoms of the molecule is complexed with HCl.

The compound of formula (I) may also be tagged with a fluorochrome or a tag known in the art. Fluorochrome can be any known in the part, such as notably rhodamine and its derivatives, or green fluorescent protein (GFP). Tags are short amino acid sequences which are specifically designed to interact with and bind to metal ions; a preferred tag is as a histidine-tag (HIS-tag or a biotin).

In the present application, the term "caspase" denotes any cysteine protease as defined above. "Caspase inhibitor" is understood as meaning any compound which is capable of inhibiting the activation of at least one caspase, in particular any compound which prevents or inhibits the process of proteolytic cleavage which allows said caspase to be obtained in active form. In particular, said caspase inhibitor prevents or inhibits the production of apoptogenic forms of the caspase in question. Demonstration of the inhibition of one or more caspases can be carried out, for example, by immunotransfer (Western blot) using antibodies specific for different forms and proforms of said caspase(s) which are supposed to be inhibited by said inhibitor. The inhibition of one or more caspase(s) can be total (in which case the active form of said caspase(s) is not detected) or only partial (said caspase(s) is(are) then detected in active form but in a reduced quantity as compared with the quantity detected in the absence of the inhibitor).

The compound of formula (I) (Q-VD-OPh negative control) according to the invention is not a caspase inhibitor. Indeed, it is classically used as a negative control for potent broad spectrum caspase inhibitor.

The compound of formula (I) is structurally very close to compound Q-VD-OPh, which is of formula (II) below:

(II)

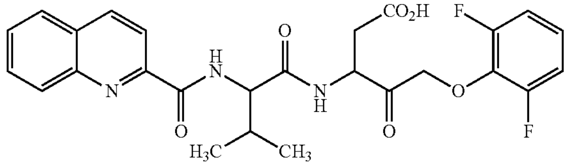

The compound of formula (I) according to the invention has a lateral chain of glutamic acid (Glu or E), instead of a lateral chain of aspartic acid (Asp or D) (as for compound of formula (II)).

Surprisingly, the compound of formula (I) according to the invention inhibits viral replication, and is a negative control for caspase inhibition, i.e. it does not show any caspase inhibitory activity. To the contrary, Q-VD-OPh (compound of formula (II)) inhibits viral replication and is a broad caspase inhibitor.

In the present application, "antiviral agent", "anti-riboviral agent" and "antiretroviral agent" are understood as meaning, respectively, any agent having an antiviral, anti-riboviral or antiretroviral effect. A ribovirus is a RNA virus, i.e. a virus which has RNA as its genetic material. Such agents include in particular antiviral, in particular anti-riboviral and in particular antiretroviral medicaments, which act on at least one step of the replication of the virus. In particular, said agents can allow viral replication to be prevented, reduced or inhibited.

The compound of formula (I) or a salt thereof according to the invention can be administered to any animal or human likely to benefit from such administration, in particular to any animal or human infected or likely to be infected by a virus as described in the present application.

As used in the present application, the term "animal" defines any non-human animal, in particular any non-human mammal, and more particularly an ape or a cat.

As used in the present application, the expressions "viral infection" and "infected by a virus" mean that said animal or human has been exposed to a pathogenic RNA or DNA virus and that said virus has attached itself to one or more cells of the host and has then penetrated (or is likely to penetrate) into said cell(s) and has had (or will possibly have) harmful effects for at least one cell of said animal or human. In particular, such a viral infection is capable of evolving into clinical signs of induced pathologies or pathologies accompanying said infection. Accordingly, a "viral infection" within the scope of the present invention includes the earliest phases of viral contamination as well as the latest phases and the intermediate phases of viral contamination. By way of example, in the case of HIV, the infection evolves in several phases which may follow one another over time. Four phases in particular are distinguished: (1) the primary infection corresponds to the phase of seroconversion which follows contamination and is (in 50 to 75% of cases) or is not accompanied by symptoms; it is followed by (2) a latent phase, then (3) a phase with minor symptoms, and finally (4) the phase of profound immunodepression or the AIDS stage, which is generally symptomatic and is generally accompanied by numerous opportunistic infections.

The term "viral infection" therefore also includes any clinical sign, symptom or disease that occurs in an animal or human (patient) following contamination of said animal or patient by a virus as described in the present application. Accordingly, the "viral infection" includes both contamination by said virus and the various pathologies which are the consequence of contamination by said virus.

The viral infections which fall within the scope of the present invention include in particular the group constituted by viral encephalitis, viral meningitis, aphthous fever, influenza, yellow fever, respiratory viral infections such as infections due to SARS or SARS-CoV-2, which include in particular coronavirus disease-19 (COVID-19), infantile diarrhoea, in particular infantile diarrhoea caused by rotavirus, haemorrhagic fevers, in particular haemorrhagic fevers caused by the Ebola virus, the dengue virus and the Lassa virus, poliomyelitis, rabies, measles, rubella, varicella, smallpox, herpes zoster, genital herpes, hepatitis, especially A, B, C, D and E, leukaemia and paralysis due to HTLV-1 (human T lymphotropic virus type 1), as well as infections caused by an HIV virus, and more particularly by HIV-1 or HIV-2, or an SIV virus, which include in particular acquired immunodeficiency syndrome (AIDS).

Preferably, the viral infections are infections by SARS (Severe Acute Respiratory Syndrome) or SARS-CoV-2 virus (Severe Acute Respiratory Syndrome Coronavirus-2), especially SARS-CoV-2, which include in particular coronavirus disease-19 (COVID-19); and infections caused by an HIV virus, and more particularly by HIV-1 or HIV-2, which include in particular acquired immunodeficiency syndrome (AIDS).

The term "prophylaxis" or "prevent a viral infection" denotes any degree of retardation in the time of appearance of clinical signs or symptoms of the viral infection, as well as any degree of inhibition of the severity of the clinical signs or symptoms of the viral infection, including, but not being limited to, the total prevention of the viral infection. This requires the compound of formula (I) or a salt thereof, or the composition or combination comprising said compound to be administered to the animal or patient likely to be contaminated by a virus before any clinical sign or symptom of the disease appears. The prophylactic administration of the compound of formula (I) or a salt thereof, or of a composition or combination comprising said compound can take place before said animal or human is exposed to the virus responsible for the viral infection, or at the time of exposure. Such a prophylactic administration serves to prevent and/or reduce the severity of any subsequent infection.

"Treatment" is understood as meaning the therapeutic effect produced on an animal or human by the active substances when they are administered to said animal or human at the time of contamination of said animal or human by the virus or after contamination. When the compound of formula (I) or a salt thereof, or a composition or combination comprising said compound, is administered to an animal or human after contamination by the virus, it can be administered during the primary infection phase, during the asymptomatic phase or after the appearance of clinical signs or symptoms of the disease. According to an embodiment, the compound of formula (I) or a salt thereof is administered during the primary infection phase. According to another embodiment, the compound of formula (I) or a salt thereof is administered after the primary infection phase, i.e. in the chronic phase (which may be asymptomatic or after the appearance of clinical signs or symptoms of the disease). According to a particular embodiment, administration takes place within 24 or 48 hours of said animal or human being exposed to said virus, as quickly as possible.

Said treatment includes any curative effect obtained by virtue of the compound of formula (I) or a salt thereof, or a composition or combination comprising said compound, and also the improvement in the clinical signs or symptoms observed in the animal or patient as well as the improvement in the condition of the animal or patient. The term includes in particular the effects obtained as a consequence of inhibiting viral replication and/or inhibiting cell death induced by the virus. Accordingly, the term "treatment" covers the slowing down, reduction, interruption and stopping of the viral infection and/or of the harmful consequences of the viral infection; treatment does not necessarily require the complete removal of all the clinical signs of the viral infection and the symptoms of the disease, nor the complete elimination of the virus.

The compound of formula (I) or a salt thereof, can therefore be administered to an animal or human at risk of developing a viral infection (prophylaxis) or after contamination by the virus has taken place, in particular after manifestation of the first clinical signs or symptoms of the disease, for example after proteins or antibodies specific to said virus have been detected in the blood of the animal or patient (treatment).

According to a particular embodiment, therefore, the compound of formula (I) or a salt thereof, is administered to an animal or human before said animal or human is exposed to said virus, during exposure to said virus or after exposure to said virus. Administration after exposure to the virus can be carried out at any time but will preferably be carried out as quickly as possible after exposure, in particular within 48 hours of the animal or human being exposed to said virus.

Furthermore, it is also possible to envisage a plurality of successive administrations of the compound of formula (I) or a salt thereof, so as to increase the beneficial effects of the treatment. In order to increase the chances of cure, or at least prolong the life expectancy of the animal or human, or the prophylactic effect, it is possible in particular to carry out one or more successive administrations of said compound before the animal or human is exposed to the virus and/or during exposure to the virus and/or after exposure to the virus, in particular within 48 hours of said animal or human being exposed to said virus.

The viruses that fall within the scope of the present invention include DNA viruses and RNA viruses (riboviruses), in particular viruses responsible for cell deficiencies such as immune deficiencies (such as AIDS), respiratory deficiencies (such as SARS and SARS-CoV-2), neuronal deficiencies (such as rabies) or epithelial deficiencies (such as haemorrhagic fevers).

More specifically, said virus is a virus selected from the following families:

- the coronaviridae, in particular the genus coronavirus, for example the SARS virus or the SARS-CoV-2 virus;
- the retroviruses, in particular those of the genus lentivirus and those of the genus oncovirus, for example the HTLV-1 virus;
- the flaviviridae, in particular those of the genus flavivirus, which includes especially the dengue virus, the yellow fever virus and the viruses responsible for viral encephalitises, such as the West Nile virus, the Japanese encephalitis virus and the Saint-Louis encephalitis virus; or in particular those of the genus hepacivirus, such as Hepatitis C virus;
- the orthomyxoviruses, which include the influenza viruses;
- the paramyxoviridae, in particular those of the genus morbillivirus, especially the measles virus, and the respiratory viruses, in particular those of the genus pneumovirus, for example human respiratory syncytial virus and metapneumovirus;
- the reoviridae, in particular the virus of the genus rotavirus;
- the picornaviridae, in particular the viruses of the genus enterovirus, including the polioviruses and the viruses responsible for viral meningitis, those of the genus aphthovirus, especially the aphthous fever virus, and those of the genus rhinovirus; or in particular the viruses of the genus hepatovirus such as Hepatitis A virus;
- the filoviridae, in particular the Ebola virus or the Marburg virus;
- the arenaviridae, in particular the Lassa virus;
- the rhabdoviridae, in particular those of the genus rhabdovirus, including the rabies virus, and the genus vesiculovirus, which includes the vesicular stomatitis virus;
- the togaviridae, in particular of the genus Rubivirus, including the rubella virus;
- the poxviridae, in particular the vaccinia and variola viruses;
- the herpesviridae, in particular the Herpes, varicella and Zoster viruses; and
- the hepadnaviridae such as the hepatitis B virus; the hepatitis D virus; or the hepeviridae such as the Hepatitis E virus.

Preferably, the viruses that fall within the scope of the present invention are RNA viruses (riboviruses).

More specifically, said RNA virus is a virus selected from the following families:

- the coronaviridae, in particular the genus coronavirus, for example the SARS virus or the SARS-CoV-2 virus;
- the retroviruses, in particular those of the genus lentivirus and those of the genus oncovirus, for example the HTLV-1 virus;
- the flaviviridae, in particular those of the genus flavivirus, which includes especially the dengue virus, the yellow fever virus and the viruses responsible for viral encephalitises, such as the West Nile virus, the Japanese encephalitis virus and the Saint-Louis encephalitis virus; or in particular those of the genus hepacivirus, such as Hepatitis C virus;

- the orthomyxoviruses, which include the influenza viruses;
- the paramyxoviridae, in particular those of the genus morbillivirus, especially the measles virus, and the respiratory viruses, in particular those of the genus pneumovirus, for example human respiratory syncytial virus and metapneumovirus;
- the reoviridae, in particular the virus of the genus rotavirus;
- the picornaviridae, in particular the viruses of the genus enterovirus, including the polioviruses and the viruses responsible for viral meningitis, those of the genus aphthovirus, especially the aphthous fever virus, and those of the genus rhinovirus; or in particular the viruses of the genus hepatovirus such as Hepatitis A virus;
- the filoviridae, in particular the Ebola virus or the Marburg virus;
- the arenaviridae, in particular the Lassa virus;
- the rhabdoviridae, in particular those of the genus rhabdovirus, including the rabies virus, and the genus vesiculovirus, which includes the vesicular stomatitis virus;
- the togaviridae, in particular of the genus Rubivirus, including the rubella virus; and
- the hepadnaviridae such as the hepatitis B virus; the hepatitis D virus; or the hepeviridae such as the Hepatitis E virus.

The present invention is directed in particular to the coronaviruses or the lentiviruses, insofar as they cause the degeneration of multiple organs.

According to a particular embodiment, said virus is a human retrovirus, in particular a human lentivirus, more particularly a human immunodeficiency (HIV) virus such as HIV-1 or HIV-2, and preferably HIV-1.

According to another particular embodiment, said virus is a simian retrovirus, in particular a simian lentivirus, and more particularly a simian immunodeficiency virus (SIV) such as the SIVmac251 or SIVmac239 virus.

According to a particular embodiment, said virus is a human coronavirus, in particular SARS-CoV-2.

The compound of formula (I) or a salt thereof according to the invention can be used to prevent, reduce and/or inhibit viral replication in an animal or human infected by a virus as defined above.

The term "viral replication" as used in the present application includes the totality of the steps of the replication cycle of the virus. Especially this term includes the main steps of replication of the retroviruses described in the present application, including entry of the virus into the cell, integration of the viral genome into the DNA of the host cell, and viral maturation.

"Viral maturation" or "maturation of the viruses" denotes, in the case of the lentiviruses and in particular in the case of the HIV viruses, the process of cleavage of the Gag polyproteins, by the viral protease, into 4 structural proteins (p17, p24, p7 and p6) and the assembly of those proteins to the matrix (p17), capsid (TCD4+ p24) and nucleocapsid (p7). Following the maturation phase, the virions, which, prior to cleavage, were not mature, are infectious, that is to say ready to infect new cells.

The prevention or inhibition of viral replication can be either partial or total.

Typically, the compound of formula (I) or a salt thereof according to the invention has the ability to prevent, reduce and/or inhibit viral replication in vitro.

The ability of the compound of formula (I) or a salt thereof according to the invention to prevent or inhibit viral replication can be evaluated, for example, in vitro, by flow cytometry, after intracellular labelling of a viral antigen such as p24, as described in the example below.

According to a particular embodiment, the compound of formula (I) or a salt thereof according to the invention is used to prevent, reduce and/or inhibit the synthesis of viral proteins in an animal or human infected by a virus as described in the present application.

The expression "viral proteins" refers to at least one protein of the virus, in particular to at least one structural protein of the virus. The viral proteins whose synthesis can be prevented, slowed, reduced and/or inhibited under the effect of the active ingredients according to the invention, in particular under the effect of said compound according to the invention, include in particular the envelope, capsid, nucleocapsid proteins, etc., especially for the lentiviruses, the proteins Gag, Pol and Env; and in particular the envelope, capsid, membrane, spike proteins, etc., especially for the coronaviruses, the proteins S (spike), M (membrane protein), E (envelope protein) and N (capside phosphoprotein).

The prevention or inhibition of the synthesis of viral proteins can be partial, or total, or partial for some of the viral proteins and total for the remainder of the viral proteins. When it is partial for all the viral proteins or for some viral proteins, the expression "prevent or inhibit the synthesis of viral proteins" means that, under the effect of the compound of formula (I) or a salt thereof according to the invention, one or more viral proteins are synthesized in a smaller quantity in the host cell, and are therefore present in a smaller quantity in the host cell or in the cell supernatant, as compared with the synthesis of the same viral proteins in the absence of said active substance(s). When the prevention or inhibition of the synthesis of viral proteins is total, the viral protein(s) is(are) not synthesized in a detectable manner.

The compound of formula (I) or a salt thereof can further be used for preventing and/or inhibiting viral replication and/or viral protein synthesis, without any significant effect on cell death. In particular it can be used for preventing and/or inhibiting viral replication, in particular viral protein synthesis, without any significant effect on the death of the T lymphocytes and more particularly of the CD4+ T cells, induced by a virus as described in the present application, in an animal or human infected by said virus.

The expression "without any significant effect on cell death" means that, in an animal or human infected by a virus as described in the present application, cell death of cells infected by said virus and treated by the compound of formula (I) or a salt thereof, is not significantly different from non-infected cells. In other words, cell death of a sample of cells of an animal or human infected by the virus and treated by the compound of formula (I) or a salt thereof, is not significantly different from a sample of non-infected cells of said animal or human.

Typically, in vitro, cell death of a sample of cells of an animal or human infected by the virus and treated by the compound of formula (I) or a salt thereof, is not significantly different from a sample of non-infected cells of said animal or human.

The percentage of cell death may be demonstrated in vitro by any laboratory technique conventionally used. For example, a simple direct cell count using a microscope will be sufficient. It may also be possible to analyze cell death by flow cytometry after an Annexin V surface staining on a given day post-infection, for example day 5 or more.

The compound of formula (I) or a salt thereof according to the invention can be used in the prophylaxis and/or treatment of a viral infection, in the primary infection phase and/or in the chronic phase (which may be asymptomatic or after the appearance of clinical signs or symptoms of the disease). The animal or human infected by the virus may be in the primary infection phase or in the chronic phase. The compound of formula (I) or a salt thereof according to the invention can also be used to prevent, reduce and/or inhibit viral replication in an animal or human infected by a virus, in the primary infection phase and/or in the chronic phase (which may be asymptomatic or after the appearance of clinical signs or symptoms of the disease).

According to a particular embodiment, the compound of formula (I) or a salt thereof can be prepared in the form of a pharmaceutical composition further comprising one or more carrier(s), diluent(s) and/or adjuvant(s) or a combination thereof, as well as other active substances. In the case of an injectable administration, there can be chosen especially a formulation in an aqueous, non-aqueous or isotonic solution.

In the present application, the term "carrier" denotes any substrate (that is to say anything which is able to transport at least one active ingredient) which does not interfere with the efficacy of the biological activity of the compound of formula (I). A large number of carriers are known in the prior art. The carriers used can be, for example, water, a saline solution, serum albumin, a Ringer solution, polyethylene glycol, water-miscible solvents, sugars, binders, excipients, pigments, vegetable or mineral oils, water-soluble polymers, surface-active agents, thickening or gelling agents, cosmetic agents, solubilizing agents, stabilizing agents, preservatives, alkalinizing or acidifying agents or a combination thereof. The formulation of such carriers in the form of a pharmaceutical composition is described especially in "Remington's Pharmaceutical Sciences", 18th edition, Mack Publishing Company, Easton, Pa.

In the present application, the term "diluent" means a diluting agent and includes soluble diluents and insoluble diluents. There is generally used an insoluble diluent when the active ingredient is soluble and a soluble diluent when the active ingredient is insoluble. An "insoluble" active ingredient can be completely insoluble in an aqueous medium or can have limited solubility (that is to say a solubility of less than 10 mg/ml in 250 ml of water at a pH of from 1.0 to 7.5) in an aqueous medium. Examples of insoluble diluents include microcrystalline cellulose, silicified microcrystalline cellulose, hydroxymethylcellulose, dicalcium phosphate, calcium carbonate, calcium sulfate, magnesium carbonate, tricalcium phosphate, etc. Examples of soluble diluents include mannitol, glucose, sorbitol, maltose, dextrates, dextrins, dextrose, etc.

The adjuvants which can be used within the scope of the invention are in particular nucleic acids, peptidoglycans, carbohydrates, peptides, cytokines, hormones or other small molecules. Said adjuvants that are used can be, for example, adjuvants of the non-methylated CpG dinucleotide (CpG) family, adjuvants of the poly IC family and adjuvants of the monophosphoryl lipid A (MPL) family or an analogue thereof.

According to a preferred embodiment, the carrier(s) or diluent(s) or combinations thereof used in the invention are pharmaceutically acceptable substances or a combination of pharmaceutically acceptable substances. A substance or a combination of substances is said to be "pharmaceutically acceptable" when it is suitable for administration to a living being (for example a human or animal) for therapeutic or prophylactic purposes. It is therefore preferably non-toxic for the host to which it is administered.

The terms "administration" and "administer" as used in the present application include any administration, whatever the chosen route of administration.

The routes of administration and the dosages vary according to a variety of parameters, for example according to the condition of the patient, the type of infection and the severity of the infection to be treated, or according to the compound of formula (I) or a salt thereof and the other antiviral agents used.

The compound of formula (I) or a salt thereof can especially be administered to an animal or human in dry form, in solid form, in particular tablet, powder, gelatin capsule, pill, granules, suppository, polymer capsule or compressed tablet, and more precisely accelerated release tablet, enteric-coated tablet or sustained release tablet; in gel form; or in the form of a solution or liquid suspension, in particular syrup, injectable, infusible or drinkable solution, microvesicles or liposomes. The compounds can also be in the form of doses in dry form, such as a powder or a lyophilisate, for reconstitution at the time of use using a suitable diluent.

According to their galenical form, the composition according to the invention, in particular the antiviral composition of the invention, can be administered by the enteral, parenteral (intravenous, intramuscular or subcutaneous), transcutaneous (or transdermal or percutaneous), cutaneous, oral, mucosal, in particular transmucous-buccal, nasal, ophthalmic, otological (in the ear), oesophageal, vaginal or rectal route, or alternatively by the intragastric, intracardiac, intraperitoneal, intrapulmonary or intratracheal routes.

In addition, the compound of formula (I) or a salt thereof can be packaged for administration in the form of a single dose (monodose) or a multiple dose (multidose). In order to increase the effects of the treatment, it is possible to carry out administration in the form of a plurality of successive administrations, repeated on one or more occasions, after a particular time interval. For example, a plurality of administrations can be carried out per day or per week.

The amount of active ingredient administered to an animal or human is a therapeutically effective amount. A "therapeutically effective amount" is an amount sufficient to obtain a significant effect and in particular to bring a significant benefit to a human or animal within the scope of an administration for prophylaxis or treatment as defined in the present application. A therapeutically effective amount is also an amount for which the beneficial effects outweigh any toxic or harmful effect of the active ingredient(s). Such an amount can correspond to an amount sufficient to significantly inhibit viral replication or to bring about the disappearance, reduction or improvement of any existing infection caused by a virus. The therapeutically effective amount varies according to factors such as the state of infection and the age, sex or weight of the animal or human individual. The dosage regimens can be adjusted in order to obtain an optimum therapeutic effect. For example, it is possible to administer from 15 to 50 mg/kg body weight of compound according to the invention. More specifically, in the case of a human weighing about 60 kg, a therapeutically effective amount of compound according to the invention can be from 100 to 300 mg/day, administered in from 1 to 3 doses.

The present invention relates also to the use of the compound of formula (I) or a salt thereof, in association with other antiviral agents, in particular other riboviral agents, in particular other antiretroviral agents, in the prophylaxis and/or treatment of a viral infection. As examples of antiviral agents there may be mentioned, in connection with infection due to HIV, the combined antiretroviral drugs within the scope of highly active antiretroviral therapy (or "HAART").

Accordingly, a particular pharmaceutical composition according to the invention further comprises at least one other antiviral agent.

The present invention therefore relates also to a novel antiviral composition comprising or consisting of:

(i) at least one compound chosen from the compound of formula (I) and its pharmaceutically acceptable salts:

(I)

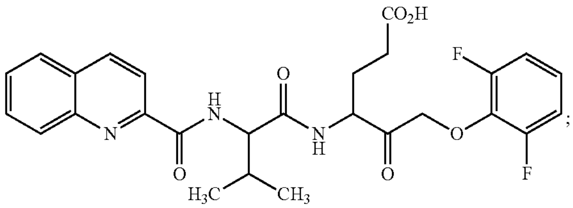

;

(ii) at least one antiviral or anti-inflammatory agent, in particular at least one antiretroviral agent, wherein said antiviral agent is different from (i).

The present invention therefore relates also to a novel antiviral composition for use for the prophylaxis and/or treatment of a viral infection, in particular in an animal or human, and more particularly for inhibiting viral replication in an animal or human infected by a virus.

The compound of formula (I) or a salt thereof can therefore be used in association with an antiviral agent or a plurality of antiviral agents (ii), in particular at least two other antiviral agents. Said other antiviral agent or agents (ii) can in particular be antiretroviral agents.

The expression "consists essentially of" as used in the present application means that other minor ingredients or molecules can be present with the active ingredients expressly listed, without affecting the activity of said active ingredients.

The antiviral and antiretroviral agents (ii) which can be used within the scope of the present application include in particular:

- transcriptase inhibitors, in particular reverse transcriptase inhibitors, for the retroviruses, which are intended to act at the very start of the viral replication cycle, especially reverse transcriptase inhibitors which are intended to act before the viral DNA becomes integrated into the DNA of the host cell and which prevent or inhibit the synthesis of proviral DNA from the viral RNA;
- viral RNA-dependent RNA polymerase modulators, such as nucleotide analogues;
- viral protease inhibitors (or antiproteases), which generally act at the end of the viral cycle, during maturation of the newly synthesized viral proteins;
- inhibitors of the fusion of the viral envelope with the cell membrane, which are intended to block the penetration of the virus into the cell;
- inhibitors of receptors or coreceptors, such as CD4 or BOB;
- antisense oligonucleotides;
- integrase inhibitors; and
- molecules that target other steps of viral multiplication (addressing, integration port).

According to a particular embodiment, said other antiviral agent or agents consist(s) of at least one transcriptase inhibitor and/or at least one viral protease inhibitor.

According to a particular embodiment, the antiviral composition according to the invention comprises, consists essentially of or consists of:

(i) at least the compound of formula (I) or a salt thereof, according to the invention, (ii) at least one transcriptase inhibitor, and (iii) at least one viral protease inhibitor.

The term "transcriptase inhibitor" as used in the present application includes in particular the nucleoside analogues, the non-nucleoside analogues and the nucleotide analogues of reverse transcriptase.

According to a particular embodiment, the transcriptase inhibitor is a reverse transcriptase inhibitor, in particular an HIV virus reverse transcriptase inhibitor, and more particularly a reverse transcriptase inhibitor selected from the group constituted by:

- the nucleoside reverse transcriptase inhibitors of HIV, in particular zidovudine or azidothymidine (AZT), didanosine or ddI, zalcitabine or ddC, stavudine or d4T, lamivudine or 3TC, abacavir or ABC, and emtricitabine or FTC;
- the non-nucleoside reverse transcriptase inhibitors of HIV, in particular nevirapine, efavirenz and delavirdine; and
- the nucleotide analogues of the reverse transcriptase of HIV, in particular tenofovir or bis-POC-PMPA.

According to a particular embodiment, one of the transcriptase inhibitors used is AZT.

According to an embodiment, the viral RNA-dependent RNA polymerase modulator is a nucleotide analogue, such as remdesivir.

The term "protease inhibitor" as used in the present application includes in particular peptidomimetic molecules and molecules of the non-peptide type. "Peptidomimetic molecules" are peptides which mimic the natural enzyme substrate and fix to the protease substrate binding sites, preventing cleavage of the protein precursors (for example Gag and Gag-Pol for HIV or SIV), which leads to the production of defective and non-infectious viral particles.

According to a particular embodiment, the viral protease inhibitor is a protease inhibitor of an HIV virus and in particular a viral protease inhibitor selected from the group constituted by the following peptidomimetic molecules: Indinavir or IDV, Nelfinavir or NLFN, Saquinavir or SQN, Ritonavir or RTN, Amprenavir, Lopinavir. According to a particular embodiment, one of the HIV viral protease inhibitors used is Indinavir.

According to a particular embodiment, at least one of the other antiviral agents according to the invention is a fusion inhibitor, in particular an HIV virus fusion inhibitor, for example enfuvirtide or umifenovir. A "fusion inhibitor" is understood as being an inhibitor which acts in the first stage of replication of the virus by preventing fusion between the viral envelope and the cell membrane, for example by competitive inhibition.

In the case of Ebola virus, SARS and SARS-CoV-2, MERS-coronavirus (MERS-CoV) and influenza virus, membrane fusion and host cell entry is mediated by transmembrane protease/serine subfamily member 2 (TMPRSS2), an airway and alveolar cell serine protease. Thus, such a fusion inhibitor may be camostat mesilate or nafamostat mesilate. The fusion inhibitor may also be an inhibitor of angiotensin-converting enzyme 2 (ACE2) or an antimalarial/parasiticide drug. ACE2 inhibitors may be used to inhibit the entry of viruses such as SARS-CoV-2, which use ACE2 as receptor for S protein-driven host cell entry. ACE2 inhibitors and antimalarial/parasiticide drugs may be chosen from chloroquine phosphate, hydroxychloroquine, cepharanthine, selamectin, mefloquine and its salts such as mefloquine hydrochloride.

The anti-inflammatory agents which can be used within the scope of the present application include in particular monoclonal antibodies.

Especially, the present invention therefore relates also to a novel antiviral composition comprising or consisting of:

(i) at least one compound chosen from the compound of formula (I) and its pharmaceutically acceptable salts:

(I)

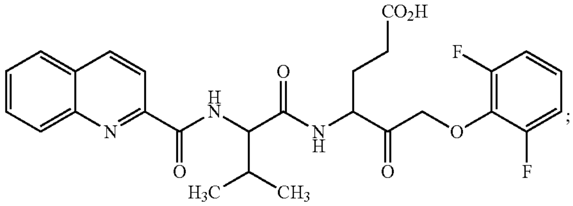

;

and (ii) at least one anti-inflammatory agent, in particular chosen from monoclonal antibodies. Said monoclonal antibodies may be directed against inflammatory interleukins and their receptors, such as IL-6 and its receptors. Preferably, the monoclonal antibody is an anti-IL6 receptor, such as tocilizumab or sarilumab; or an anti-IL-6, preferably siltuximab. Such an antiviral composition may be used for the prophylaxis and/or treatment of a coronavirus infection, such as SARS-CoV-2 infection.

According to a particular embodiment, said antiviral composition can further comprise one or more carrier(s), diluent(s) and/or adjuvant(s) or a combination thereof as defined in the present application.

Another aspect of the present invention relates to the compound of formula (I) or a salt thereof, for use in increasing a prophylactic or therapeutic effect of one or more other antiviral or anti-inflammatory agents as defined in the present application and/or in reducing the amount of the other antiviral or anti-inflammatory agents administered to a human or animal.

According to another aspect of the present invention, the active ingredients are combined in a combination for use in an antiviral therapy.

Accordingly, the present invention relates also to products comprising or consisting of:

(i) at least one compound chosen from the compound of formula (I) and its pharmaceutically acceptable salts:

(I)

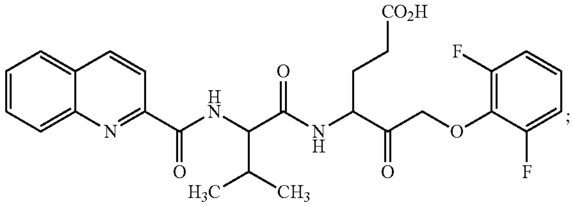

;

and (ii) at least one antiviral or anti-inflammatory agent, in particular at least one antiretroviral agent, different from compound (i), as a combined preparation for simultaneous, separate or sequential use in antiviral therapy; or for simultaneous, separate or sequential use for the prophylaxis and/or treatment of a viral infection.

Constituents (i) and (ii) form a functional unit by virtue of a common indication, which is the implementation of an antiviral treatment.

Such a combined therapy is intended most particularly for the prophylaxis and/or treatment of viral infections in a human or animal infected by a virus as defined in the present application.

The term "simultaneously" and the expression "simultaneous use" mean that compounds (i) and (ii) of said combination are administered at the same time, at the same moment, to a human or animal.

According to a particular embodiment, compounds (i) and (ii) of said combination are administered separately or sequentially. They are then employed, administered separately, without prior mixing, in several (at least two) dosage forms (for example two distinct capsules). Said combination therefore corresponds to a presentation of the compound(s) (i) on the one hand and of the compound(s) (ii) on the other hand, in distinct compositions.

In the case where compounds (i) and compounds (ii) are administered sequentially in terms of time, the sequence of administration is not important, it being possible for administration of compound(s) (i) to precede or follow administration of compound(s) (ii). According to a particular embodiment, compound (i) or at least one of compounds (i) is administered before compound (ii) or at least one of compounds (ii) is administered. Alternatively, compound (ii) or at least one of compounds (ii) can be administered before compound (i) or at least one of compounds (i) is administered.

The expression "sequential use" means that said or one of said compounds (i) and said or one of said compounds (ii) of the combination according to the invention are administered not simultaneously but separately in terms of time, one after the other.

The term "precede" or "preceding" is used when a compound (or a plurality of compounds) of the combination according to the invention is administered a few minutes or several hours, or even several days, prior to administration of the other compound(s) of said combination. Conversely, the term "follow" or "following" is used when a compound (or a plurality of compounds) of the combination according to the invention is administered a few minutes or several hours, or even several days, after administration of the other compound(s) of said combination.

Furthermore, according to a particular embodiment, compounds (i) and (ii) of the combination according to the invention are formulated for administration at an interval of one or several hours, preferably a 1-, 2-, 3- or 4-hour interval, more preferably a 1- or 2-hour interval, yet more preferably a 1-hour interval.

The compound(s) (i) and the compound(s) (ii) of the combination can be formulated to facilitate their ingestion and, in particular, can be formulated with one or more carrier(s), diluent(s) or adjuvant(s) as defined above, or a combination thereof.

In addition, the compound(s) (i) and the compound(s) (ii) of the combination according to the invention can be administered by the same route of administration or, on the other hand, by distinct routes of administration. The possible galenical forms and routes of administration are those described above.

The present invention relates also to an antiviral composition according to the invention for use as a medicament, in particular as an antiviral agent and more particularly as an antiretroviral agent. More precisely, said antiviral composition or said combination can be used in the prophylaxis and/or treatment of a viral infection, in particular an infection caused by a virus as defined in the present application, and more particularly for inhibiting viral replication, in a mammal or human.

The present invention relates also to the use of an antiviral composition according to the invention in the production of a pharmaceutical composition for the prophylaxis and/or treatment of a viral infection, in particular an infection caused by a virus as defined in the present application, in a mammal or human.

The invention relates also to a method of treating an animal or human infected by a virus as described in the present application, said method comprising at least one step of administration of the compound of formula (I) or a salt thereof according to the invention.

Said treatment method is, in particular, suitable for and intended for use in the prophylaxis and/or treatment of a viral infection, in particular in a human or animal infected by a virus as defined in the present application.

More precisely, said treatment method can be used to prevent and/or inhibit viral replication in an animal or human infected by a virus.

DESCRIPTION OF THE DRAWINGS

The compound Q-VE-OPh of the invention is also called "QVG" (wherein G states for glutamic acid) in FIGS. 1 and 2.

Flow cytometry analysis after intracellular staining of the viral capsid protein P24 in CD4 T lymphocytes infected with the laboratory viral strain, the HIV-1 lai in the presence of the various molecules added at the concentration of 20 μM each 2 days. Uninfected CD4 T cells served as a negative control. The staining was performed on day 5 and day 6 post-infection (PI).

Figure 2:
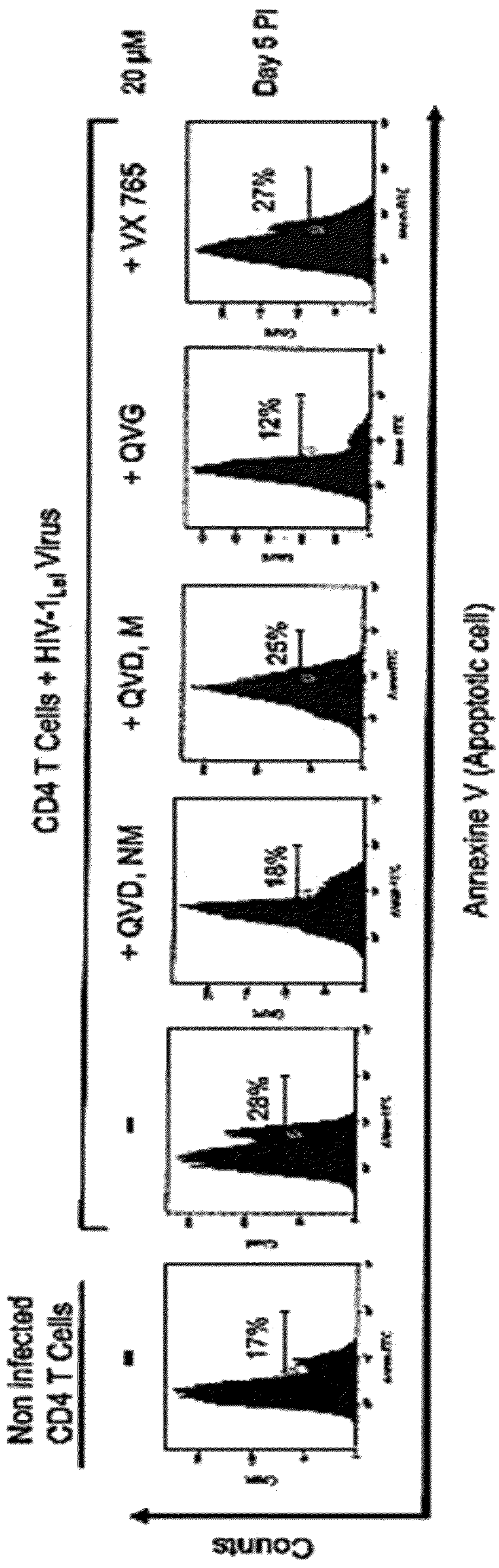

FIG. 2: The Q-VE-OPh molecule of the invention inhibits the viral replication of HIV-1 and therefore saves CD4 T cells from death:

Flow cytometry analysis of Annexin V staining carried out on CD4 T lymphocytes infected with the laboratory viral strain, the HIV-1 lai in the presence of the various molecules added at the concentration of 20 μM each 2 days. Uninfected CD4 T cells served as a control. The staining was performed on day 5 post-infection (PI).

Figure 3:
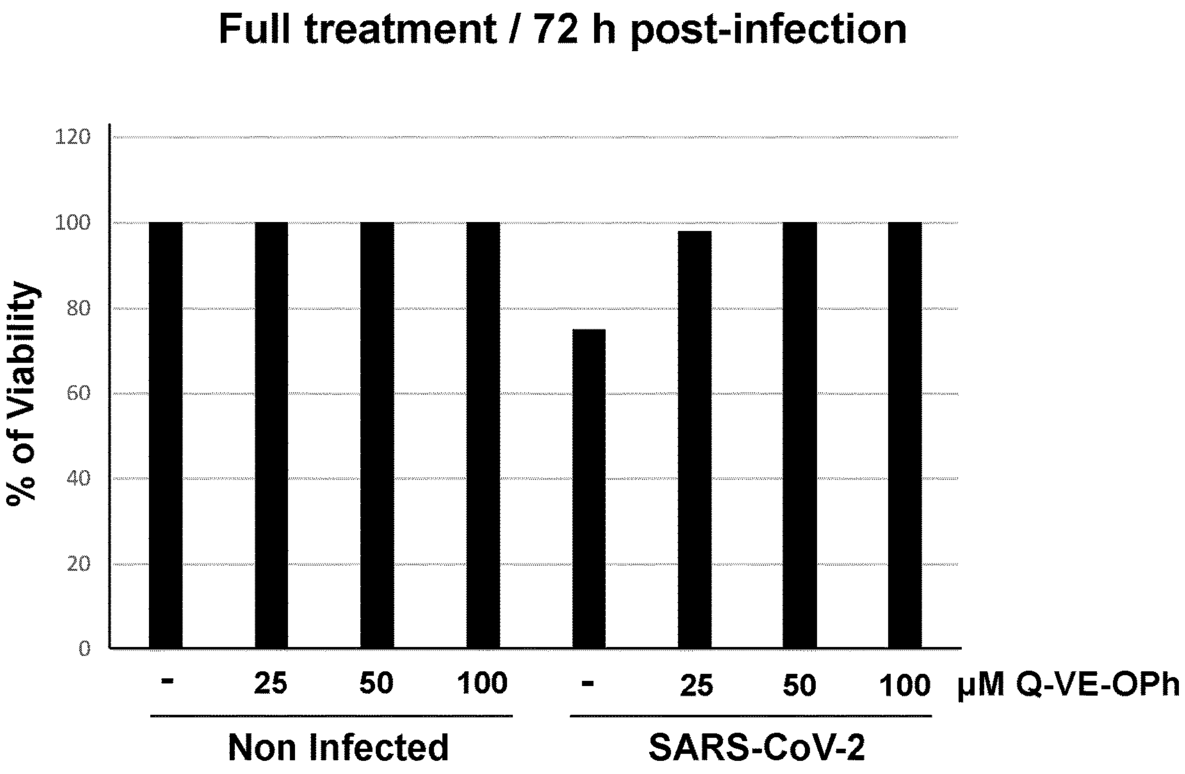

FIG. 3: Toxicity test for Q-VE-OPh on Vero E6 cells:

Vero E6 cells non infected (NI) or infected with the virus at MOI 0.05 and incubated with different concentrations of Q-VE-OPh (25 μM, 50 μM, 100 μM) were collected at day 72 h post-infection from each well, washed twice with PBS before viability fixable dye staining for 30 min at 4° C. Cells were washed after and fixed with 2% Paraformaldehyde (FPA) and then analyzed on a Fortessa Flux Cytometre. 30 000 events were recorded for each conditions in triplicate. Analyses were done later using a FlowJo Software and the percentages of viability were calculated according to the analysis report from the results of the triplicate of each condition. Results represent mean+SD (n=4) independent experiments with 3 independent point for each conditions separately.

Figure 4:
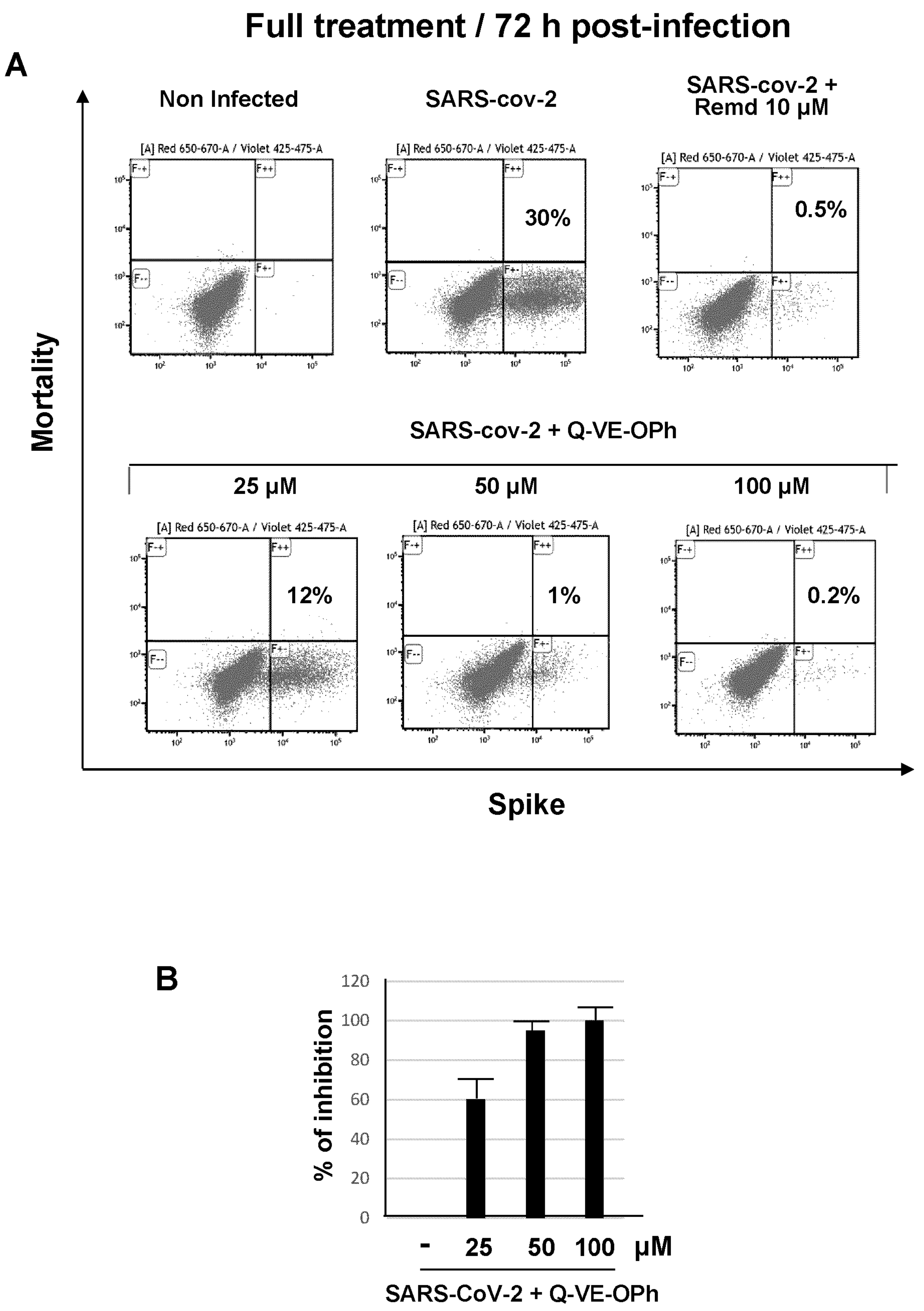

FIG. 4: Effect of Q-VE-OPh on infection and mortality induce by SARS-CoV-2 during full treatment condition. Flow cytometry analysis for the detection of Sars-CoV-2 Spike (S) protein expression in infected cells and Western blot analysis for the detection of Sars-CoV-2 Spike (S) and nucleocapsid (N) proteins expression:

A) Vero E6 cells non infected (NI) or infected with the virus at MOI 0.05 were incubated with different concentrations of Q-VE-OPh (25 μM, 50 μM, 100 μM) or Remdesivir (Rem 10 μM) for 1 h, before the infection with the virus at MOI=0.05 for 72 h. Afterwards, the cells were cultured with drug-containing medium until the end of the experiment (Full treatment) without removing the virus from the culture. After 72 h post-infection, cells were collected and stained for mortality and infection rate analysis. The % of infection is represented in each plot of analysis.

B) Results represent mean+SEM of the % of inhibition of the expression of the Spike protein staining as compared to the untreated control group (n=3).

C) Vero E6 cells were pre-treated with Q-VE-OPh at the indicated concentrations or Remdesivir (Remd 10 μM) in the same conditions described in A). A well with non-infected cells was performed as a negative control of the infection. At 72 h post-infection, cells were lysed by RIPA buffer and western blot analysis was performed to detect the expression of the Spike protein (S), the full length and S1 domain, and the Nucleocapsid protein (N). GAPDH was used as loading control. Results represent mean±SD, from 4 independent experiments with 3 independent point per condition.

Figure 5:
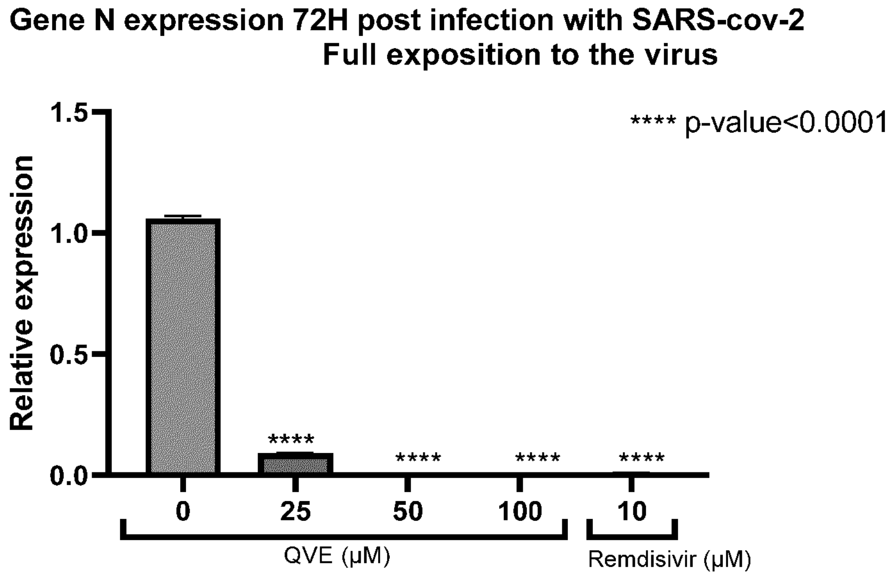
Figure 5:
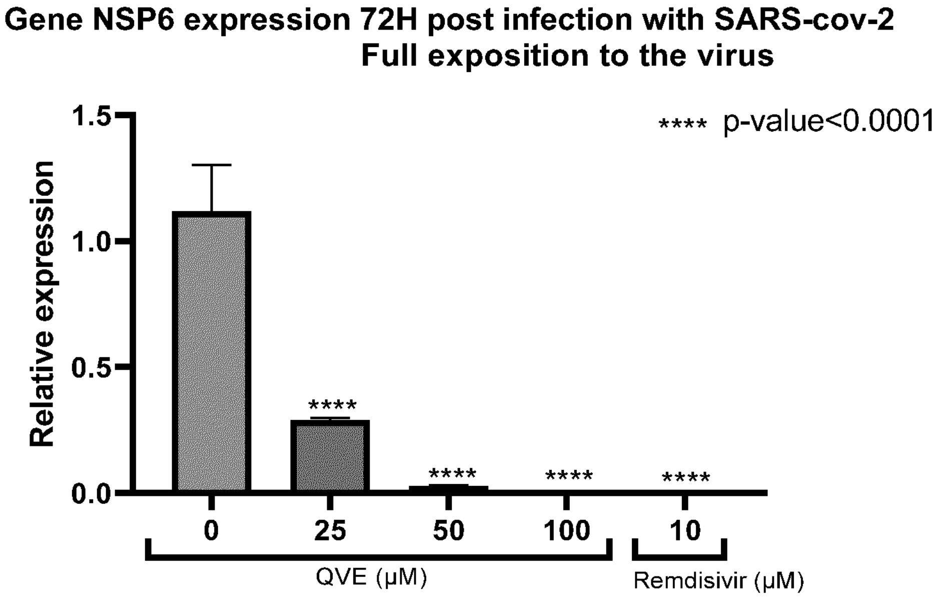

FIG. 5: The antiviral activity of Q-VE-OPh against SARS-CoV-2 in vitro during full treatment condition. Virus yield in the infected cell supernatants was quantified by qRT-PCR:

A-B) Vero E6 cells were pre-treated with Q-VE-OPh peptide ("QVE") at the indicated concentrations for 1 h, before the infection with the virus at MOI=0.05. Afterwards, the cells were cultured with drug-containing medium until the end of the experiment (Full treatment). At 72 h post-infection, supernatants were collected, and viral RNA was extracted. Real-time PCR analysis was performed on supernatant using probes against either the SARS-CoV-2 N and NSP6 genes. Results represent mean+SEM (n=3). Comparisons differences between means were explored using One-way ANOVA test followed by Dunnett's post-hoc test. ***$p<0.001$ compared to the untreated group. (Remdesivir=Remdisivir)

Figure 6:
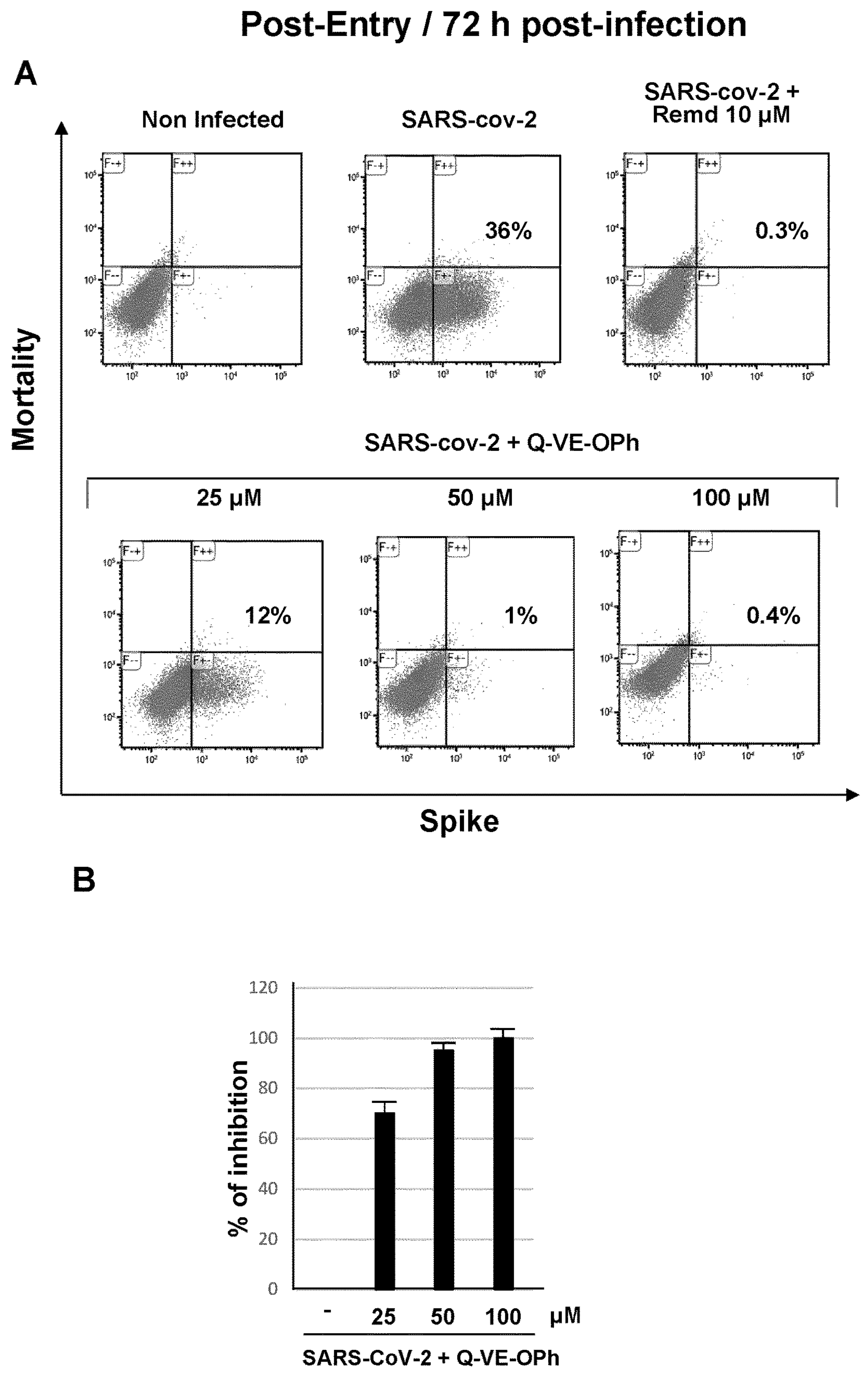

FIG. 6: Effect of Q-VE-OPh on infection and mortality induce by SARS-CoV-2 in Post-entry condition. Flow cytometry analysis for the detection of Sars-CoV-2 Spike (S) protein expression in infected cells and Western blot analysis for the detection of Sars-CoV-2 Spike (S) and Nucleocapsid (N) proteins expression:

A) Vero E6 were infected with the virus at MOI 0.05 for 2 hours and then the virus was removed from the medium. Then, the cells were incubated with different concentrations of Q-VE-OPh (25 μM, 50 μM, 100 μM) or Remdesivir (Remd 10 μM) for 72 hours (Post-Entry). The drugs were added each day at the different concentrations medium until the end of the experiment. After 72 h post-infection cells were collected and stained for mortality and infection rate analysis. The % of infection is represented in each plot of analysis.

B) Results represent mean+SEM of the % of inhibition of the expression of the Spike protein staining as compared to the untreated control group (n=3).

C) Vero E6 cells were infected then treated with Q-VE-OPh at the indicated concentrations or Remdesivir (Remd 10 μM) in the same conditions described in A). A well with non-infected cells was performed as a negative control of the infection. At 72 h post-infection, cells were lysed by RIPA buffer and western blot analysis was performed to detect the expression of the Spike protein (S), the full length and S1 domain, and the Nucleocapsid protein (N). GAPDH was used as loading control. Results represent mean±SD, from 4 independent experiments with 3 independent point per condition.

Figure 7:
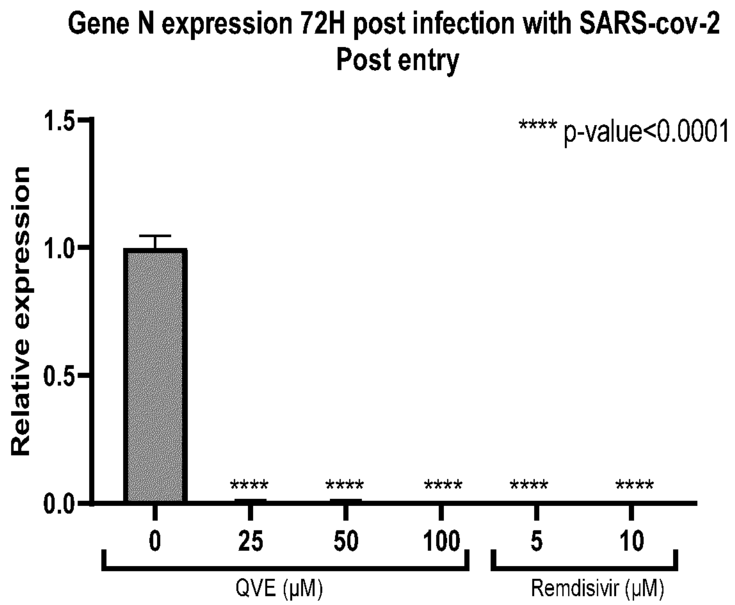
Figure 7:
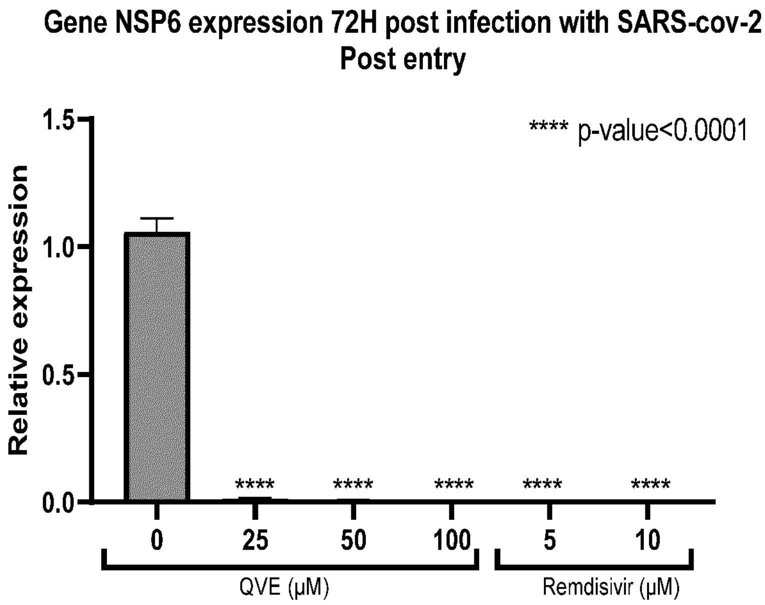

FIG. 7: The antiviral activity of Q-VE-OPh against SARS-CoV-2 in vitro for the Post-entry condition. Virus yield in the infected cell supernatants was quantified by qRT-PCR:

A-B) Vero E6 cells were infected by the virus at MOI=0.05 for 2 hours. After, the virus was removed from the medium. Then, the cells were incubated with different concentrations of Q-VE-OPh (QVE, 25 μM, 50 μM, 100 μM) or Remdesivir (Remdisivir, 10 uM) for 72 hours (Post-Entry). The drugs were added each day at the different concentrations medium until the end of the experiment. At 72 h post-infection, supernatants were collected, and viral RNA was extracted. Real-time PCR analysis was performed on supernatant using probes against either the SARS-CoV-2 N and NSP6 genes. Results represent mean+SEM (n=3). Comparisons differences between means were explored using One-way ANOVA test followed by Dunnett's post-hoc test. ***p<0.001 compared to the untreated group.

Figure 8:
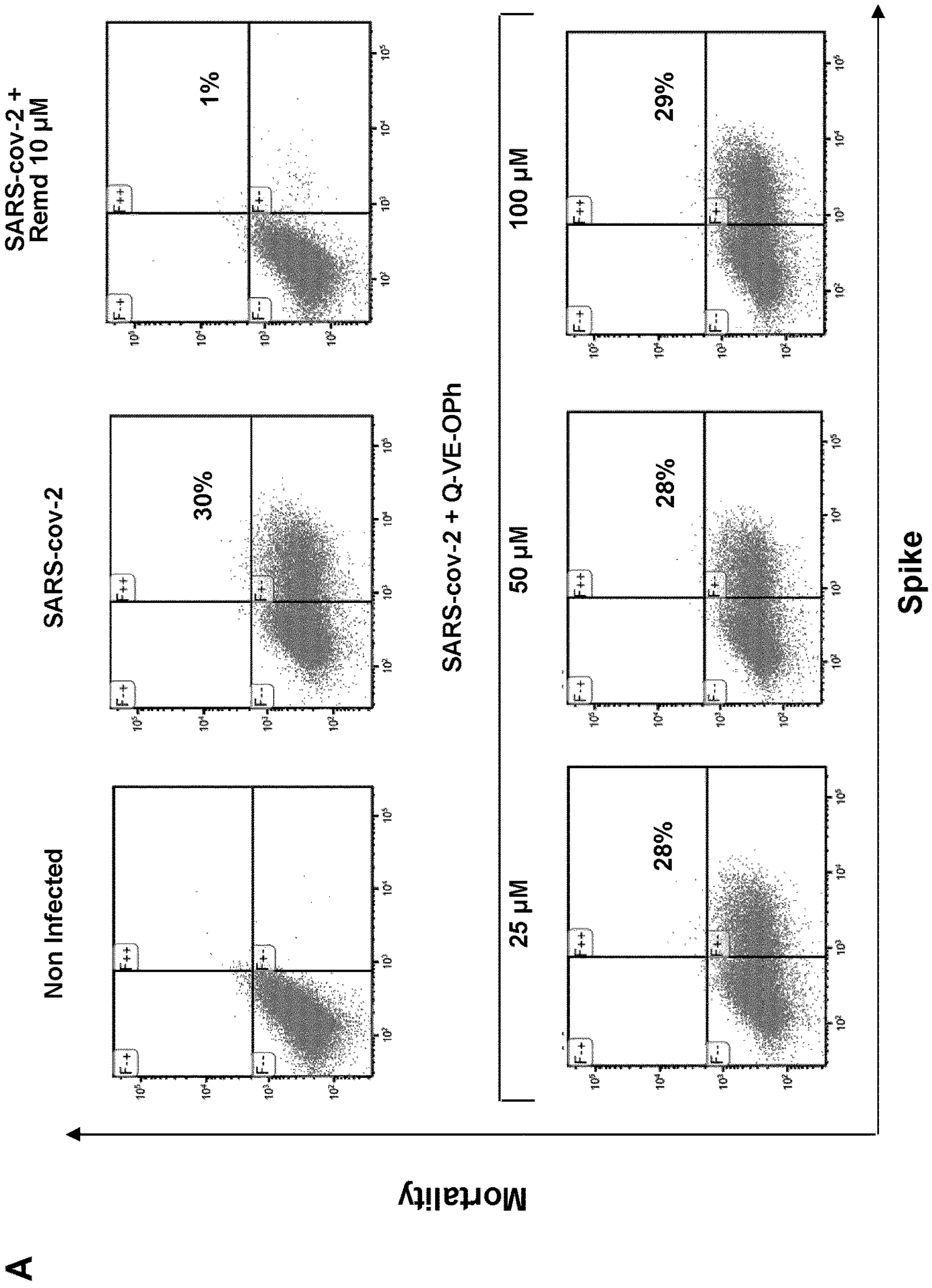

FIG. 8: Effect of Q-VE-OPh on infection and mortality induce by SARS-CoV-2 in Entry condition. Flow cytometry analysis for the detection of Sars-CoV-2 Spike (S) protein expression in infected cells and Western blot analysis for the detection of Sars-CoV-2 Spike (S) and Nucleocapsid (N) proteins expression:

A) Vero E6 cells non infected (NI) or infected with the virus at MOI 0.05 were incubated with different concentrations of Q-VE-OPh (25 μM, 50 μM, 100 μM) or Remdesivir (Remd 10 μM) for 1 h, before the infection with the virus at MOI=0.05 for 2 h. Afterwards, medium containing virus and drug were removed and replace by fresh medium without any treatment until the end of the experiment (Entry). After 72 h post-infection, cells were collected and stained for mortality and infection rate analysis. The % of infection is represented in each plot of analysis.

B) Vero E6 cells were pre-treated with Q-VE-OPh at the indicated concentrations or Remdesivir (Remd 10 μM) for 1 h before infection in the same conditions described in A). A well with non-infected cells was performed as a negative control of the infection. At 72 h post-infection, cells were lysed by RIPA buffer and western blot analysis was performed to detect the expression of the Spike protein (S), the full length and S1 domain, and the Nucleocapsid protein (N). GAPDH was used as loading control. Results represent mean±SD, from 4 independent experiments with 3 independent point per condition.

EXAMPLE 1

The compound Q-VE-OPh of the invention has been tested comparatively to other molecules for its antiviral effect against HIV virus.

The tested molecules in this assay are:

Q-VE-OPh (Q-VD-OPh negative control): compound of formula (I) of the invention,

Q-VD-OPh (Non methylated form, "QVD-Unmethylated") (caspase inhibitor): comparative, Q-VD-OPh (methylated form, "QVD-methylated") (caspase inhibitor): comparative, and VX-765 (Caspase-1 inhibitor): comparative.

Protocol

CD4 T lymphocytes isolated from blood of healthy donors and sorted with magnetic beads (TCD4 isolation kits from Miltenyi) were cultured in the absence or in the presence of HIV-1 lai virus (strain virus used in the laboratory). After 24 hours of infection, the cells were activated by Concanavalin A (ConA) at the concentration of 5 g/ml and Il-2 (100 U/ml) for 6 days. The different molecules have been added at the concentration of 20 μM to the cell culture directly after infection in each condition. The same dose of each molecule was added to the cells every two days.

Results

To detect the effects of Q-VE-OPh of the invention on the viral replication in the CD4 T lymphocytes, the inventors assessed flow cytometry analysis with intracellular staining for the viral capsid protein, P24 at day 4, 5 and 6 post-infection. In addition, a mortality test against apoptosis was performed on day 5 with Annexin V-FITC.

I—Q-VE-OPh of the Invention Inhibits the Viral Replication of the HIV Virus

The antiviral effect of Q-VE-OPh was measured by measuring the intracellular P24 capsid protein production. The different molecules QVD-methylated, QVD-Unmethylated, Q-VE-OPh as well as the VX-765 were added at the dose of 20 μM every two days from the first day of infection on the T CD4 activated cells in culture.

Flow cytometric analyzes for the detection of the capsid viral protein P24 were carried out. The results of the experiments show that the Q-VE-OPh molecule of the invention, which has no anti-caspase activity, has the same antiviral effect as the comparative Q-VD-OPh molecule (methylated or non-methylated form). This is the first time that these tests have been conducted and show these results.

Figure 1:
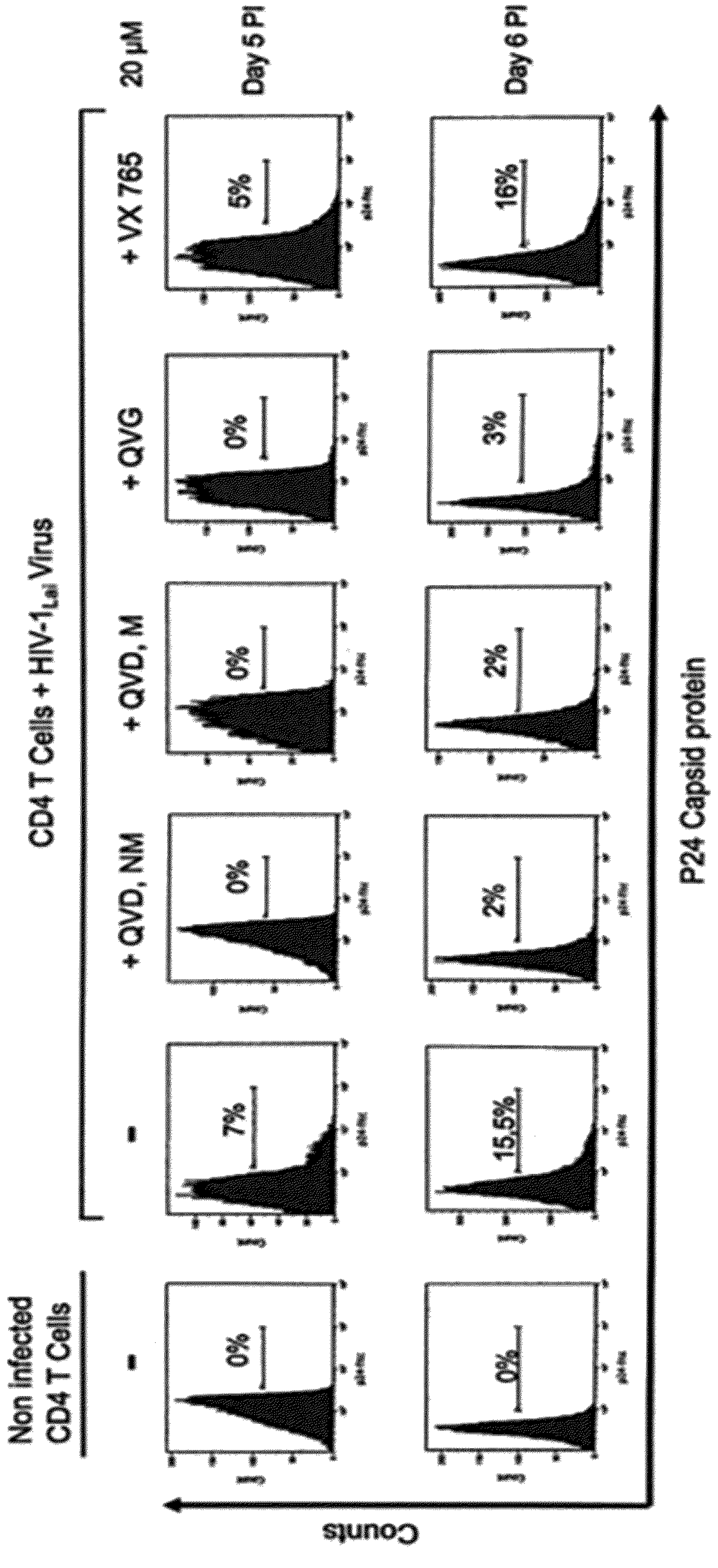
FIG. 1: Compound Q-VE-OPh of the invention has an antiviral effect on HIV-1 replication in vitro.

It is a very interesting result because it proves that the antiviral activity of the QVD molecule is independent of its anti-caspase activity. The inhibitor VX-765, which is a specific caspase-1 inhibitor, has no effect on the viral replication of the HIV virus. Compound Q-VE-OPh of the invention has an antiviral effect on HIV-1 replication in vitro (FIG. 1).

II—Q-VE-OPh of the Invention Reduces Cell Death or the Apoptosis of CD4 T Cells

The HIV-1 virus kills the infected CD4 T cells by apoptosis, and therefore cell mortality has been analyzed by flow cytometry after an Annexin V surface staining on day 5 post-infection in all conditions.

The results show that the cells in the presence of the Q-VE-OPh molecule of the invention show much less mortality than the infected cells or than cells in the presence of the caspase-1 inhibitor VX-765, and even better than the non-infected cells. The results were the same for QVD-Unmethylated, contrary to QVD-methylated.

These results prove that the CD4 T lymphocytes are preserved from cell death because they are not infected (protection by the antiviral effect of the molecule) and not because of the caspase inhibition, because the Q-VE-OPh molecule of the invention has no anti-caspase activity. The Q-VE-OPh molecule of the invention inhibits the viral replication of HIV-1 and therefore saves CD4 T cells from death (FIG. 2).

CONCLUSION

These results show for the first time an effect of Q-VE-OPh of the invention for the inhibition of the viral replication of the HIV-1 virus. These results are very important because Q-VE-OPh is the negative control for the caspase activity of the Q-VD-OPh molecule, and for the first time it is shown that the antiviral effect of Q-VD-OPh is not due to its function of inhibiting caspases. Indeed, the above results show that this antiviral activity can be maintained by a negative control molecule devoid of any caspase inhibition activity (Q-VE-OPh of the invention).

EXAMPLE 2

Materials & Methods

Cells, Virus and Drugs

African green monkey kidney Vero E6 cell line was obtained kindly from Dr Andreola Marie-Aline, University of Bordeaux, and maintained in Eagle's medium (Dulbecco's modified Eagle's medium; Gibco Invitrogen supplemented with 10% heat-inactivated FBS, 1% PS (Penicillin 10,000 U/ml; Streptomycin 10,000 μg/ml) (Gibco Invitrogen) at 37° C. in a humidified atmosphere of 5% CO2. The strain BetaCoV/France/IDF0372/2020 was supplied by the National Reference Centre for Respiratory Viruses hosted by Institut Pasteur (Paris, France) and headed by Pr. Sylvie van der Werf. The human sample from which strain BetaCoV/France/IDF0372/2020 was isolated has been provided by Dr. X. Lescure and Pr. Y. Yazdanpanah from the Bichat Hospital, Paris, France. Moreover, the strain BetaCoV/France/IDF0372/2020 was supplied through the European Virus Archive goes Global (Evag) platform, a project that has received funding from the European Union's Horizon 2020 research and innovation program under grant agreement No 653316. The virus titer used for all the experiments was $4\times10^6$ PFU/mL. All the infection experiments were performed in a biosafety level-3 (BLS-3) laboratory at the CRC (Cordelier Research Center). Q-VE-OPh was purchased from Clinisciences (Cat no. 1171, Biovision) and Remdesivir from COGER (Cat no. AG—CR1-3713-M005).

Evaluation of Antiviral Activities, Toxicity and Infection Inhibition

To evaluate the toxicity of the Q-VE-OPh on Vero E6 Cells and the antiviral efficacy, the inventors measured by flux cytometry the % of mortality and the % of infected cells. Cells were cultured overnight in 24-well cell-culture petridish with a density of $75\times10^4$ cells/well. The next day, cells were pretreated for 1 h with the different doses of the indicated Q-VE-OPh or Remdesivir. Then, the virus was subsequently added at MOI 0.05 to allow infection for 1 h in 250 l/well. After 1 h, complete media was added to cell culture to a final volume of 500 μl/well. Drugs were added each day at same concentration to cell culture. At 72 h post infection, the cell supernatant was collected and frozen immediately at −80° C. for viral extraction and q-PCR amplification. The cells were collected and a part was used to flux cytometry analysis to measure the inhibition of the infection by an intra-cellular staining against Spike protein (SARS-CoV-2 Spike Protein-Alexa 647, Cat no. 51-6490-82, eBioscience) using a Cytofix/cytoperm fixation permeabilization kit (Cat no. 554714, BD) according to the manufacturer's instructions. Toxicity was analyzed by using Viability 405/452 Fixable Dye (Cat no. 130-109-814, from Miltenyi Biotec) according to the manufacturer's instructions. Briefly, the cells were washed twice with PBS before viability fixable dye staining for 30 min at 4° C. Then, the cells were permeabilized by the Cytofix/cytoperm buffer for 20 min, and after two washes with the permawash buffer, the anti-spike-Alexa 647 was added to the cells for 30 min at 4° C. After the staining, the cells were fixed with 2% paraformaldehyde (FPA) and then analyzed on a Fortessa Flux Cytometer. 30 000 events were recorded for each conditions in triplicate. Analyses were done later using a FlowJo Software. The other part of the cells was lysed in RIPA lysis buffer (Invitrogen, Cat no. 10230544) containing protease (Roche) and phosphatase inhibitors (Invitrogen) for further quantification and immunoblotting analysis. Each condition was done in triplicate (n=3) in the same experiment and repeated for 3 independent experiments.

Time-of-Addition Experiment of Q-VE-OPh

The Q-VE-OPh (25, 50 and 100 μM) of the invention, and Remdesivir (10 μM), were used for the time-of-addition experiment. Vero E6 cells ($5\times10^4$ cells/well) were treated with Q-VE-OPh, Remdesivir, or DMSO at different stages of virus infection. For "Full-time" treatment, Vero E6 cells were pre-treated with the drugs for 1 h prior to virus infection, followed by incubation with virus for 2 h in the presence of the drugs until the end of the experiment. For "Entry" treatment, the drugs were added to the cells for 1 h before virus infection, and maintained during the 2-h viral attachment process. Then, the virus-drug mixture was replaced with fresh culture medium without drugs until the end of the experiment. For "Post-entry" experiment, virus was added to the cells to allow infection for 2 h, and then virus-containing supernatant was replaced with drug-containing medium until the end of the experiment. The experimental condition of the DMSO-treatment group was consistent with that of the "Full-time" group. For all the experimental groups, cells were infected with virus at an MOI of 0.05, and at 72 h p.i., cell supernatant and cell lysates were collected for qRT-PCR and Western blot analysis, respectively. Cells were also analyzed by flux cytometry for mortality and viral replication by analyzing the intracellular expression of the spike protein.

Viral RNA Extraction and Quantitative Real-Time RT-PCR (qRT-PCR)

Two hundred microliter cell culture supernatant was harvested for viral RNA extraction using the MiniBEST Viral RNA/DNA Extraction Kit (Takara, Cat no. 9766) according to the manufacturer's instructions. RNA was eluted in 30 μL RNAase Free water. Total RNA was converted to cDNA using PrimeScript RT Reagent Kit with gDNA Eraser (Takara, Cat no. RR047A), following the manufacturer's recommended procedures. Quantitative PCR was performed using TB Green Premix Ex Taq II (Takara Cat no.RR820A). Briefly, each reaction consisted of a total volume of 25 μl containing 1 μL of each primer [0.4 μM/μL], 2 μl of cDNA (5 ng/μL), 12.5 μl TB Green Premix Ex Taq II and 8.5 μL of Rnase free Water. Real-time PCR was performed using Bio Rad CFX384 Real-Time system PCR Machine. The thermal cycling conditions used were as follows: initial denaturation: 95° C. for 30 seconds, followed by 40 cycles of amplification at 96° C. for 5 seconds, and 60° C. for 30 seconds. The primers used for SARS-CoV-2 N and NSP6 genes designed and described by Abdel-Sater et al (Jan. 29, 2021; A Rapid and Low-Cost protocol for the detection of B.1.1.7 lineage of SARS-CoV-2 by using SYBR Green-Based RT-qPCR. medRxiv preprint doi: https://doi.org/10.1101/2021.01.27.21250048) were purchased from Eurofins:

```
N-qF:
                                        (SEQ ID NO: 1)
CGTTTGGTGGACCCTCAGAT

N-qR:
                                        (SEQ ID NO: 2)
CCCCACTGCGTTCTCCATT

NSP6-qF:
                                        (SEQ ID NO: 3)
GGTTGATACTAGTTTGTCTGGTTTT

NSP6-qR:
                                        (SEQ ID NO: 4)
AACGAGTGTCAAGACATTCATAAG.
```

SARS-CoV-2 cDNA (Ct~20 for N and NSP6 genes) was used as a positive control. Calculated Ct values were converted to fold-reduction of treated samples compared to control using the ΔCt method (fold changed in viral RNA=2^ΔCt).

Western Blot Analysis

For Western blot analysis, protein samples were separated on 4-12% NUPAGE SDS-PAGE (Invitrogen) and then transferred onto nitrocellulose membranes (Amersham Bioscience). After being blocked with 5% BSA in TBS buffer containing 0.05% Tween 20, the blot was probed with the mouse anti-Spike antibody (S1-NTD) (E7M5X) (1/2000, Ozyme, Cat. No. 42172S) and the anti-N antibody (1:10 000 dilution, Fisher scientific, Cat. No. MA536086) on primary antibodies and the horseradish peroxidase (HRP)-conjugated Goat-Anti-Mouse IgG or Goat-Anti-Rabbit IgG (Invitrogen) as the secondary antibody, respectively. Protein bands were detected by ECL Chemiluminescent substrate (Pierce) using a CCD camera (Syngene Pxi-4).

Statistics Analysis

Statistics analysis between means were explored using One-way ANOVA test followed by Dunnett's post-hoc test to determine significance was performed using GraphPad Prism software (GraphPad Software Inc., USA). Values are given as means±S.E.M. and a p-value <0.05% was considered significant.

Results

Treatments with different concentrations of Q-VE-OPh peptide have shown no toxicity effect on Vero E6 cells whether they were infected or not with the virus at MOI 0.05 for 72 h post-infection (FIG. 3).

The antiviral and mortality effects of different concentrations of Q-VE-OPh were evaluated by flux cytometry analysis using intracellular staining against SARS-Cov-2 spike proteins and the viability dye to measure the mortality. Remdesivir was used as a positive control during the study.

Results show that Q-VE-OPh inhibits the viral replication of the SARS-CoV-2 after its entry in the cell (post-entry antiviral effect) at the dose of 25 μM (inhibition is around 70%), and the inhibition is complete at the concentration of 50 μM (inhibition is around 99%). This effect was seen with a daily dose of 50 μM during 72 h post-infection. Q-VE-OPh treatments were able to reduce significantly the expression of the viral Spike and Nucleocapsid proteins within infected cells; this reduction was comparable to that obtained with Remdesivir (FIGS. 4, 6). Indeed, Q-VE-OPh treatments were able to reduce significantly the relative expression of the Nucleocapsid (N) protein (structure protein) and the accessory protein ORF6 (NSP6) genes in the supernatants of infected cells for full treatment and post-entry conditions (FIG. 5, 7).

However, no significant effect of Q-VE-OPh on the entry of the virus into the cell during infection was observed, whatever the dose used (FIG. 8).

These findings demonstrate that the Q-VE-OPh according to the invention is highly effective in the control of SARS-CoV-2 infection in vitro by inhibiting the viral replication inside the cell and by preventing viral production and new infections without any toxicity, even at the concentration of 100 μM added for three days.

The invention claimed is:

1. A method of preventing or treating an infection caused by a virus in a subject in need thereof, comprising administering to the subject a therapeutically effective amount of a compound of formula (I) and/or a pharmaceutically acceptable salt thereof:

(I)

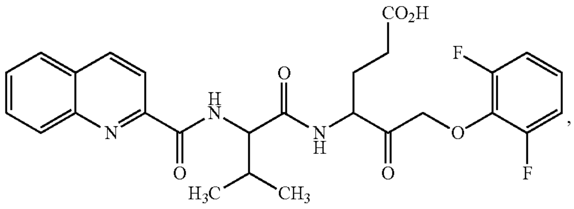, wherein the virus is a retrovirus or a coronavirus.

2. The method according to claim 1, wherein said viral infection is caused by a DNA virus or an RNA virus.

3. The method according to claim 2, wherein said virus is a virus selected from the following families:

the coronaviridae; and the retroviridae.

4. The method according to claim 1, wherein said virus is a human retrovirus.

5. The method according to claim 1, wherein said viral infection is selected from the group consisting of a respiratory viral infection caused by a coronavirus, leukaemia and paralysis due to HTLV-1 (human T lymphotropic virus type 1), an infection caused by an HIV virus, or an infection caused by an SIV virus.

6. The method according to claim 1, wherein the method prevents and/or reduces and/or inhibits viral replication in an animal or human infected by said virus.

7. The method according to claim 1, wherein the method prevents and/or reduces and/or inhibits viral protein synthesis in an animal or human infected by said virus.

8. The method according to claim 1, wherein said compound does not have any significant effect on cell death.

9. The method according to claim 1, in which said subject is a non-human mammal.

10. A method of preventing or treating an infection caused by a virus in a subject in need thereof, comprising administering to the subject a therapeutically effective amount of a composition comprising as active ingredient the compound according to claim 1 and further comprising one or more carrier(s), diluent(s) or adjuvant(s) or a combination thereof, wherein the virus is a retrovirus or a coronavirus.

11. The method according to claim 10, characterized in that it is formulated for administration by the enteral, parenteral, transcutaneous, cutaneous, oral, mucosal, intragastric, intracardiac, intraperitoneal, intrapulmonary or intratracheal routes.

12. The method according to claim 3, wherein the coronaviridae is a coronavirus; and the retroviridae is a lentivirus or oncovirus.

13. The method according to claim 12, wherein the coronavirus is a SARS virus or a SARS-CoV-2 virus; and the lentivirus or oncovirus is an HTLV-1 virus, an HIV virus, or an SIV virus.

14. The method of claim 9, wherein the non-human mammal is an ape or a cat.

* * * * *